United States Patent
Uneyama et al.

(10) Patent No.: US 10,181,414 B2
(45) Date of Patent: Jan. 15, 2019

(54) INDICATOR USED IN ELECTRONIC DEVICE MANUFACTURING APPARATUS AND METHOD FOR DESIGNING AND/OR MANAGING THE APPARATUS

(71) Applicant: SAKURA COLOR PRODUCTS CORPORATION, Osaka-shi, Osaka (JP)

(72) Inventors: Kazuhiro Uneyama, Osaka (JP); Seisaku Oshiro, Osaka (JP)

(73) Assignee: SAKURA COLOR PRODUCTS CORPORATION, Osaka-shi (JP)

( * ) Notice: Subject to any disclaimer, the term of this patent is extended or adjusted under 35 U.S.C. 154(b) by 133 days.

(21) Appl. No.: 14/897,461

(22) PCT Filed: Aug. 4, 2014

(86) PCT No.: PCT/JP2014/070419
§ 371 (c)(1),
(2) Date: Dec. 10, 2015

(87) PCT Pub. No.: WO2015/025699
PCT Pub. Date: Feb. 26, 2015

(65) Prior Publication Data
US 2016/0141192 A1     May 19, 2016

(30) Foreign Application Priority Data
Aug. 22, 2013  (JP) ................................ 2013-172322

(51) Int. Cl.
*H01L 21/67* (2006.01)
*C09D 11/50* (2014.01)
(Continued)

(52) U.S. Cl.
CPC ...... *H01L 21/67253* (2013.01); *C09D 11/037* (2013.01); *C09D 11/50* (2013.01);
(Continued)

(58) Field of Classification Search
CPC .............. H01L 21/67253; C09D 11/50; G01N 21/775; G01N 21/78; G01N 21/783;
(Continued)

(56) References Cited

U.S. PATENT DOCUMENTS 3,568,627 A   3/1971 Selinger et al.
4,155,895 A   5/1979 Rohowetz et al.
(Continued)

FOREIGN PATENT DOCUMENTS

CN   1877777 A    12/2006
CN   101014668 A   8/2007
(Continued)

OTHER PUBLICATIONS

Office Action dated Mar. 14, 2017, issued in counterpart Chinese Application No. 201480033301.2, with partial English translation. (11 pages).
(Continued)

*Primary Examiner* — David Zarneke
(74) *Attorney, Agent, or Firm* — Westerman, Hattori, Daniels & Adrian, LLP

(57) ABSTRACT

Provided is an indicator that can easily detect whether treatment with at least one member of plasma, ozone, ultraviolet rays, and radical-containing gas is uniformly performed on an entire substrate in an electronic device manufacturing apparatus; also provided is a method for designing and/or managing an electronic device manufacturing apparatus using the indicator. The indicator is used in an electronic device manufacturing apparatus, wherein (1) the indicator detects at least one member selected from the group consisting of plasma, ozone, ultraviolet rays, and radical-containing gas, (2) the indicator has a shape that is the same as that of a substrate used in the electronic device manufacturing apparatus, (3) the indicator contains a color- (Continued)

changing layer, and (4) the color-changing layer is formed by an ink composition whose color changes or disappears by reaction with at least one member selected from the group consisting of plasma, ozone, ultraviolet rays, and radical-containing gas.

10 Claims, 3 Drawing Sheets

(51) Int. Cl.
| | |
|---|---|
| G01N 21/77 | (2006.01) |
| G01N 21/78 | (2006.01) |
| G01N 21/85 | (2006.01) |
| G01N 31/22 | (2006.01) |
| G01N 33/00 | (2006.01) |
| G01N 33/50 | (2006.01) |
| C09D 11/037 | (2014.01) |
| H01J 37/32 | (2006.01) |

(52) U.S. Cl.
CPC .......... *G01N 21/78* (2013.01); *G01N 21/783* (2013.01); *H01J 37/32935* (2013.01)

(58) Field of Classification Search
CPC ......... G01N 2021/8528; G01N 31/223; G01N 33/0039; G01N 33/52; Y10T 436/206664
See application file for complete search history.

(56) References Cited

U.S. PATENT DOCUMENTS

| | | | |
|---|---|---|---|
| 4,179,397 A | 12/1979 | Rohowetz et al. | |
| 4,448,548 A | 5/1984 | Foley | |
| 4,839,311 A | 6/1989 | Riley et al. | |
| 5,955,025 A | 9/1999 | Barrett | |
| 5,990,199 A | 11/1999 | Bealing et al. | |
| 6,063,631 A | 5/2000 | Ignacio | |
| 6,117,685 A * | 9/2000 | Omatsu | G01N 31/225 422/416 |
| 6,238,623 B1 | 5/2001 | Amhof et al. | |
| 6,267,242 B1 | 7/2001 | Nagata et al. | |
| 6,355,448 B1 | 3/2002 | Foltz et al. | |
| 6,410,338 B1 | 6/2002 | Lippold et al. | |
| 6,524,763 B1 | 2/2003 | Kuroda et al. | |
| 6,659,036 B2 | 12/2003 | Omatsu et al. | |
| 6,852,281 B2 * | 2/2005 | Inoue | G01N 31/223 422/416 |
| 7,189,355 B2 | 3/2007 | Mikumo et al. | |
| 7,213,534 B2 | 5/2007 | Siikaluoma et al. | |
| 7,364,700 B2 * | 4/2008 | Maruo | G01N 31/225 422/83 |
| 7,364,770 B2 | 4/2008 | Nagashima et al. | |
| 7,976,781 B2 * | 7/2011 | Maruo | G01N 21/783 422/86 |
| 7,981,687 B2 * | 7/2011 | Yamaguchi | G01N 31/223 106/163.01 |
| 8,222,327 B2 | 7/2012 | Mikumo et al. | |
| 8,343,437 B2 | 1/2013 | Patel | |
| 8,530,242 B2 * | 9/2013 | Lin | C23C 14/54 137/551 |
| 8,567,338 B2 | 10/2013 | Greene et al. | |
| 9,168,086 B2 | 10/2015 | Allen | |
| 9,194,808 B2 | 11/2015 | Yamaguchi et al. | |
| 9,944,061 B2 | 4/2018 | Garhart | |
| 2001/0054374 A1 | 12/2001 | Omatsu et al. | |
| 2002/0051733 A1 | 5/2002 | Antonoplos et al. | |
| 2002/0121629 A1 | 9/2002 | Mikumo et al. | |
| 2005/0054374 A1 | 3/2005 | Namiki | |
| 2006/0194056 A1 | 8/2006 | Nagashima et al. | |
| 2006/0244379 A1 | 11/2006 | Shin | |
| 2006/0283746 A1 | 12/2006 | Sutoh et al. | |
| 2008/0090726 A1 | 4/2008 | Eskra et al. | |
| 2008/0267811 A1 | 10/2008 | Yamaguchi et al. | |
| 2009/0212237 A1 | 8/2009 | Sugiki et al. | |
| 2010/0119410 A1 | 5/2010 | Yamaguchi et al. | |
| 2011/0009535 A1 | 1/2011 | Mikumo et al. | |
| 2011/0065203 A1 | 3/2011 | Studer et al. | |
| 2011/0275159 A1 | 11/2011 | Landgrebe et al. | |
| 2011/0312096 A1 | 12/2011 | Whitman et al. | |
| 2012/0100395 A1 | 4/2012 | Feiler et al. | |
| 2012/0315659 A1 | 12/2012 | Andreescu et al. | |
| 2014/0154808 A1 * | 6/2014 | Patel | G01K 3/04 436/1 |
| 2015/0050745 A1 | 2/2015 | Karato et al. | |
| 2016/0045631 A1 | 2/2016 | Yamaguchi et al. | |
| 2016/0133444 A1 * | 5/2016 | Oshiro | C09D 11/033 216/60 |
| 2016/0141192 A1 | 5/2016 | Uneyama et al. | |
| 2016/0349222 A1 * | 12/2016 | Mori | H01J 37/32917 |
| 2017/0044389 A1 * | 2/2017 | Mori | H01L 21/3065 |
| 2017/0101548 A1 * | 4/2017 | Mori | A61L 2/14 |
| 2017/0153174 A1 * | 6/2017 | Yamakawa | G01N 21/255 |
| 2017/0261476 A1 * | 9/2017 | Hishikawa | C09D 11/50 |
| 2017/0330777 A1 | 11/2017 | Hishikawa et al. | |

FOREIGN PATENT DOCUMENTS

| | | |
|---|---|---|
| EP | 1312918 A2 | 5/2003 |
| GB | 2 168 082 A | 6/1986 |
| JP | 63-36786 A | 2/1988 |
| JP | S63-36876 A | 2/1988 |
| JP | 1-295423 A | 11/1989 |
| JP | 4-305492 A | 10/1992 |
| JP | 6-69165 A | 3/1994 |
| JP | 11-37988 A | 2/1999 |
| JP | 2000-269191 A | 9/2000 |
| JP | 2001-174449 A | 6/2001 |
| JP | 2001-237097 A | 8/2001 |
| JP | 2001-242249 A | 9/2001 |
| JP | 2002-011081 A | 1/2002 |
| JP | 2002-22534 A | 1/2002 |
| JP | 2002-502953 A | 1/2002 |
| JP | 2002-303618 A | 10/2002 |
| JP | 2002/322315 A | 11/2002 |
| JP | 2002-323451 A | 11/2002 |
| JP | 2003-506156 A | 2/2003 |
| JP | 2003-325646 A | 11/2003 |
| JP | 2004-101488 A | 4/2004 |
| JP | 2004-146738 A | 5/2004 |
| JP | 2004-146739 A | 5/2004 |
| JP | 2004-203984 A | 7/2004 |
| JP | 2004-298479 A | 10/2004 |
| JP | 2005-111154 A | 4/2005 |
| JP | 2005-142287 A | 6/2005 |
| JP | 2005-315828 A | 11/2005 |
| JP | 2005-329019 A | 12/2005 |
| JP | 2006-078463 A | 3/2006 |
| JP | 2006-223351 A | 8/2006 |
| JP | 2007-40785 A | 2/2007 |
| JP | 2008-125760 A | 6/2008 |
| JP | 2009-213609 A | 9/2009 |
| JP | 2010-501655 A | 1/2010 |
| JP | 2011-530085 A | 12/2011 |
| JP | 2012-050664 A | 3/2012 |
| JP | 2012-68811 A | 4/2012 |
| JP | 2012-78202 A | 4/2012 |
| JP | 2013-95764 A | 5/2013 |
| JP | 2013-95765 A | 5/2013 |
| JP | 2013-98196 A | 5/2013 |
| JP | 2013-233387 A | 11/2013 |
| JP | 2014-109523 A | 6/2014 |
| JP | 2016-111063 A | 6/2016 |
| WO | 98/46279 A1 | 10/1998 |
| WO | 98/46994 A1 | 10/1998 |
| WO | 99/39754 A1 | 8/1999 |
| WO | 01/10476 A1 | 2/2001 |
| WO | 2004-087222 A2 | 10/2004 |
| WO | 2006/109726 A1 | 10/2006 |
| WO | 2008/022952 A1 | 2/2008 |
| WO | 2013/129473 A1 | 9/2013 |
| WO | 2014/038612 A1 | 3/2014 |

(56) References Cited

FOREIGN PATENT DOCUMENTS

| WO | 2014/196440 A1 | 12/2014 |
| WO | 2015/025699 A1 | 2/2015 |
| WO | 2015/170592 A1 | 11/2015 |

OTHER PUBLICATIONS

International Search Report dated Sep. 16, 2014, issued in counterpart Application No. PCT/JP2014/070419 (2 pages).
ISR dated Jul. 14, 2015 issued in International Application No. PCT/JP2015/062244 (2 pp).
Non-Final Office Action dated Mar. 1, 2018, issued in U.S. Appl. No. 15/305,822, (7 pp).
Notice of Allowance dated Mar. 22, 2018, issued in U.S. Appl. No. 15/316,980, (18 pp).
English Translation of JP2002/303618, Oct. 2002; (14 pp) cited in Non-Final Office Action dated Mar. 1, 2018 for U.S. Appl. No. 15/305,822.
English Translation of JP 2004/101488, Apr. 2004 (9 pp) cited in Non-Final Office Action dated Mar. 1, 2018 for U.S. Appl. No. 15/305,822.
English Translation of WO 2014/038612, Mar. 2014 (10 pp) cited in Non-Final Office Action dated Mar. 1, 2018 for U.S. Appl. No. 15/305,822.
Janus Green B, no date available; https://pubchem.ncbi.nlm.nih.gov/compound/Janus_green_B (17 pp) cited in Non-Final Office Action dated Mar. 1, 2018 for U.S. Appl. No. 15/305,822.
Bakelite BKUA 2370, Georgia Pacific Chemicals Phenolic Resins, no date available, http://www.brenntag.com/specialties/en/product-industries/industries/material-science/composites-and-advanced-materials/georgia-pacific-phenolic-resins-dispersions-composites.jsp (3 pp) cited in Non-Final Office Action dated Mar. 1, 2018 for U.S. Appl. No. 15/305,822.
Sylowhite SM 405, Jul. 2009, http://novana.ch/news/8/3/0/sylowhite-sm-405 (1 page) cited in Non-Final Office Action dated Mar. 1, 2018 for U.S. Appl. No. 15/305,822.
Final Office Action dated Nov. 17, 2017, issued in U.S. Appl. No. 15/305,822 (13 pages).
International Search Report dated Apr. 14, 2015, issued in counterpart International Application No. PCT/JP2015/053742 (1 page).
Masaaki Nagatsu, Plasma Sterilization, Journal of Plasma and Fusion Research, 2007, vol. 83, No. 7, pp. 601-606.
Notice of Allowance dated Nov. 22, 2017, issued in U.S. Appl. No. 15/316,980 (15 pages).
Final Office Action dated Nov. 17, 2017, issued in U.S. Appl. No. 14/895,835 (18 pages).
International Search Report dated Sep. 2, 2014, issued in Application No. PCT/JP2014/064209 (4 pages).
English translation of Written Opinion dated Nov. 17, 2015, issued in counterpart Application No. PCT/JP2015/073769 (4 pages).
International Search Report dated Nov. 17, 2015, issued in Application No. PCT/JP2015/073769 (3 pages).
Non-Final OA dated Jun. 28, 2017, issued in U.S. Appl. No. 14/895,835 (19 pages).
Non-Final OA dated Jun. 30, 2017, issued in U.S. Appl. No. 15/316,980 (20 pages).
International Search Report dated Jul. 14, 2015, issued in counterpart International Application No. PCT/JP2015/061545 (4 pages).
Non-Final OA dated Jul. 3, 2017, issued in U.S. Appl. No. 15/305,822 (11 pages).
International Search Report dated Feb. 9, 2016, issued in counterpart Application No. PCT/JP2015/082841 (2 pages).
Office Action dated Jun. 9, 2010, issued in counterpart Japanese Application No. 2005-064179 (2 pages).
International Search Report dated May 17, 2005, issued in Application No. PCT/JP2005/006138 (1 page).
Non-Final Office Action dated Mar. 4, 2009, issued in U.S. Appl. No. 10/594,587 (9 pages).
Final Office Action dated Nov. 27, 2009, issued in U.S. Appl. No. 10/594,587 (11 pages).
Non-Final OA dated Jun. 11, 2010, issued in U.S. Appl. No. 10/594,587 (6 pages).
Final Office Action dated Dec. 23, 2010, issued in U.S. Appl. No. 10/594,587 (5 pages).
Notice of Allowance dated Apr. 1, 2011, issued in U.S. Appl. No. 10/594,587 (7 pages).
Final Office Action dated Nov. 17, 2017, issued in U.S. Appl. No. 15/305,822 (9 pages).
Non-Final Office Action dated Dec. 19, 2017, issued in U.S. Appl. No. 15/309,510 (16 pages).
Non-Final Office Action dated Jan. 31, 2018, issued in U.S. Appl. No. 15/529,382 (25 Pages).
Office Action dated Mar. 20, 2018, issued in counterpart Japanese Application No. 2014-087638, with English translation (9 pages).
Non-Final Office Action dated May 17, 2018, issued in U.S. Appl. No. 15/117,601 (28 pages).
Final Office Action dated May 25, 2018, issued in U.S. Appl. No. 15/529,382, (37 pages).
Kitaoka, "Guide for Coating to Synthetic Resin", May 25, 1974, First Edition, pp. 212-213, with English translation, cited in Japanese Office Action dated Aug. 21, 2018.
"Toryo Genryo Binran [Paint Material Handbook]", Japan Paint Manufacturers Association, May 31, 1999, 7th Edition, pp. 77-79, with English translation, cited in Japanese Office Action dated Aug. 21, 2018.
Office Action dated Aug. 21, 2018, issued in Japanese application No. 2014-087638, with English translation (7 pages).
Final Office Action dated Sep. 20, 2018, issued in U.S. Appl. No. 15/117,601 (21 pages).
Office Action dated Aug. 22, 2018, issued in counterpart Japanese Application No. 2015-532792, with English translation (6 pages).
Office Action dated Sep. 5, 2018 issued in Chinese application No. 201580020478.3, with English translation. (12 pages).
Office Action dated Oct. 9, 2018, issued in Japanese Application No. 2015-562838, with English translation (5 pages).
Office Action dated Oct. 9, 2018, issued in Japanese Application No. 2014-244414, with English translation (7 pages).
Final Office Action dated Oct. 29, 2018, issued in U.S. Appl. No. 15/117,601 (15 pages).
Office Action dated Dec. 4, 2018, issued in counterpart Japanese Application No. 2015-095244, with English translation (5 pages).

\* cited by examiner

Condition A

Condition B

INDICATOR USED IN ELECTRONIC DEVICE MANUFACTURING APPARATUS AND METHOD FOR DESIGNING AND/OR MANAGING THE APPARATUS

TECHNICAL FIELD

The present invention relates to an indicator used in an electronic device manufacturing apparatus, and a method for manufacturing and/or managing the apparatus.

BACKGROUND ART

Various treatments are conventionally performed on substrates (substrates to be treated) to produce electronic devices. For example, when the electronic device is a semiconductor, a semiconductor wafer (wafer) is supplied, and then an insulating film or a metal film is grown (film-forming process), a photoresist pattern is formed (photolithography process), the film is processed using the photoresist pattern (etching process), a conductive layer is formed on the semiconductor wafer (impurity-adding process; also referred to as doping or diffusion process), and the uneven surface of the film is polished to be flat (CMP (chemical mechanical polishing) process). After these processes, a semiconductor wafer electrical property test is conducted to check the finish of the pattern and the electrical properties. (These processes are also generically referred to as "the pre-process.") Thereafter, semiconductor chips are formed (post-process).

In addition to the above processes, the pre-process includes a cleaning process using plasma, ozone, ultraviolet rays, etc.; a photoresist-pattern removal process using plasma, radical-containing gas, etc. (also referred to as ashing or incineration removal); and other processes. Examples of the film-forming process include CVD, by which a film is formed by chemical reaction with reactive gas on the wafer surface, and sputtering, by which metal films are formed. Examples of the etching process include dry etching by chemical reaction in plasma and etching by ion beam. Plasma refers to gas in an ionized state in which ions, radicals, and electrons are present.

In the pre-process, the wafer in-plane uniformity of each treatment is important for the following reason. Since a plurality of semiconductor chips are formed on a semiconductor wafer, if the in-plane uniformity deteriorates, this causes variation in the performance of each chip, and affects the yield. Accordingly, the in-plane uniformity of each treatment is confirmed by a method in which the above treatments are performed separately, and the wafer in-plane uniformity of each treatment is evaluated. Then, the process conditions are optimized. The uniformity of plasma itself can be evaluated by, for example, a method in which a Langmuir probe is placed in the apparatus to measure the physical constants of the plasma. The variation in the space is evaluated by sweeping the probe position. Alternatively, there is a method in which the generated plasma is analyzed by using emission spectrometry to measure excited species generated in the plasma. The distribution in the space in each field of view is evaluated by changing the measurement field of view.

CITATION LIST

Patent Literature

PTL 1: JP2001-237097A
PTL 2: JP2000-269191A

SUMMARY OF INVENTION

Technical Problem

As described above, it is necessary to uniformly perform the above treatment (treatment with at least one member selected from the group consisting of plasma, ozone, ultraviolet rays, and radical-containing gas) on an entire semiconductor wafer in a semiconductor manufacturing apparatus. In the manufacture of electronic devices other than semiconductors, such as light emitting diodes (LEDs), solar cells, liquid crystal displays, organic EL (electro-luminescence) displays, semiconductor lasers, and power devices, it is also necessary to uniformly perform the above treatment on an entire substrate. However, the above-mentioned method for confirming whether the above treatment is uniformly performed on an entire substrate by actually carrying out the treatment, and separately measuring the characteristics of the obtained films, processing accuracy, etc., has the problem of requiring considerable effort and time to confirm the uniformity (from a series of treatments to evaluation).

Moreover, the method for confirming the uniformity using a Langmuir probe requires the installation of the probe, which is not originally provided in the apparatus, in the apparatus. An apparatus held with a vacuum requires an operation of installing the probe once air is released. Further, since the probe is inserted into the space where the process is performed, the probe causes a physical block. Thus, it may be necessary to remove the probe again when the above treatment is actually performed. There is a problem of requiring considerable effort and time from the preparation to the completion of the measurement.

Furthermore, in the technique of evaluating the uniformity by performing plasma emission spectrometry using a spectrometer, a measuring device does not cause a physical block. However, since the measurement is limited to measurement from a window provided in the apparatus, it is difficult to measure the entire plasma if the inside of the apparatus cannot be looked over. Thus, the effect is limited.

In addition, in the Langmuir probe method and plasma emission spectrometry, the influence of each treatment on the in-plane distribution in the substrate (e.g., a semiconductor wafer) is not directly observed, and thus, analysis operations based on the measurement results are required.

On the other hand, these operations of confirming the uniformity cannot be omitted, because they are essential for the designing of each of the above electronic device manufacturing apparatuses, and for the management in the process using the above apparatuses.

Accordingly, there has been a demand for the development of technology capable of easily detecting whether the above treatment is uniformly performed on an entire substrate.

An object of the present invention is to provide an indicator that can easily detect whether treatment with at least one member selected from the group consisting of plasma, ozone, ultraviolet rays, and radical-containing gas is uniformly performed on an entire substrate in an electronic device manufacturing apparatus, and also to provide a method for designing and/or managing the apparatus using the above indicator.

Solution to Problem

The present inventors conducted extensive research to achieve the above object, and consequently found that the object can be achieved by using a specific technique. Thus, the present invention has been completed.

Specifically, the present invention relates to an indicator used in an electronic device manufacturing apparatus, and a method for manufacturing and/or managing the apparatus, as described below.

1. An indicator used in an electronic device manufacturing apparatus, wherein:

(1) the indicator detects at least one member selected from the group consisting of plasma, ozone, ultraviolet rays, and radical-containing gas;

(2) the indicator has a shape that is the same as that of a substrate used in the electronic device manufacturing apparatus;

(3) the indicator contains a color-changing layer; and (4) the color-changing layer is formed by an ink composition whose color changes or disappears by reaction with at least one member selected from the group consisting of plasma, ozone, ultraviolet rays, and radical-containing gas.

2. The indicator according to item 1, which is used in an electronic device manufacturing apparatus that performs at least one process selected from the group consisting of oxidation, nitriding, film formation, impurity addition, cleaning, and etching, on the substrate.

3. The indicator according to item 1 or 2, which contains a non-color-changing layer whose color does not change or disappear by reaction with at least one member selected from the group of consisting of plasma, ozone, ultraviolet rays, and radical-containing gas.

4. The indicator according to any one of items 1 to 3, wherein the color-changing layer is formed adjacent to at least one main surface of a base material.

5. The indicator according to item 3, wherein:

the non-color-changing layer and the color-changing layer are sequentially formed on a base material;

the non-color-changing layer is formed adjacent to a main surface of the base material; and the color-changing layer is formed adjacent to a main surface of the non-color-changing layer.

6. A method for designing and/or managing an electronic device manufacturing apparatus, wherein:

(1) the designing and/or managing method comprises the step of placing an indicator that detects at least one member selected from the group consisting of plasma, ozone, ultraviolet rays, and radical-containing gas under treatment with at least one member selected from the group consisting of plasma, ozone, ultraviolet rays, and radical-containing gas;

(2) the indicator has a shape that is the same as that of a substrate used in the electronic device manufacturing apparatus;

(3) the indicator contains a color-changing layer; and (4) the color-changing layer is formed by an ink composition whose color changes or disappears by reaction with at least one member selected from the group consisting of plasma, ozone, ultraviolet rays, and radical-containing gas.

7. The designing and/or managing method according to item 6, wherein the step of placing the indicator under the treatment is performed in an electronic device manufacturing apparatus that performs at least one process selected from the group consisting of oxidation, nitriding, film formation, impurity addition, cleaning, and etching, on the substrate.

The indicator used in an electronic device manufacturing apparatus, and the method for designing and/or managing the apparatus, according to the present invention are described in detail below. In the present specification, the term "electronic device" refers to a semiconductor, a light emitting diode (LED), a semiconductor laser, a power device, a solar cell, a liquid crystal display, or an organic EL display.

Indicator of the Present Invention

The indicator of the present invention is used in an electronic device manufacturing apparatus and is characterized in that:

(1) the indicator detects at least one member selected from the group consisting of plasma, ozone, ultraviolet rays, and radical-containing gas;

(2) the indicator has a shape that is the same as that of a substrate used in the electronic device manufacturing apparatus;

(3) the indicator contains a color-changing layer; and (4) the color-changing layer is formed by an ink composition whose color changes or disappears by reaction with at least one member selected from the group consisting of plasma, ozone, ultraviolet rays, and radical-containing gas. This indicator can easily detect (i.e., directly perceive) whether treatment with at least one member selected from the group consisting of plasma, ozone, ultraviolet rays, and radical-containing gas (hereinafter also referred to simply as "the treatment") is uniformly performed on an entire substrate, such as a semiconductor wafer. For example, when the substrate is a semiconductor wafer, the in-plane uniformity of the above treatment on semiconductor wafers is important in view of the recent trend to obtain a larger number of semiconductor chips from one semiconductor wafer by increasing the diameter of semiconductor wafers for cost savings. The indicator of the present invention can easily detect the in-plane uniformity. Accordingly, it is not necessary to add unnecessary wiring or measuring instruments to an apparatus that performs the above treatment, and evaluation can be conducted in the same manner as in general substrates. Moreover, design guidelines for electronic device manufacturing apparatuses can be obtained. Furthermore, the process management of the manufacturing process can be simplified, thus improving the yield of electronic devices.

The indicator of the present invention contains a color-changing layer formed by an ink composition whose color changes or disappears by reaction with at least one member selected from the group consisting of plasma, ozone, ultraviolet rays, and radical-containing gas, and may also contain a base material and various layers such as a non-color-changing layer. The color-changing layer of the present invention includes a layer whose color changes to another color, and also includes a layer whose color fades or disappears. The indicator of the present invention is described in detail below.

Base Material

The indicator of the present invention may have a base material.

The color-changing layer can typically be formed by applying or printing the above ink composition on a base material. Any base material can be used as the base material insofar as the color-changing layer can be formed on it. Examples of base materials include metals or alloys, ceramics, quartz, concrete, plastics (polyethylene terephthalate (PET), polypropylene, nylon, polystyrene, polysulfone, polycarbonate, polyimide, etc.), fibers (non-woven fabric, woven fabric, other fibrous sheets), and composite materials thereof. Synthetic resin fiber paper (synthetic paper), such as polypropylene synthetic paper or polyethylene synthetic paper, can also be suitably used. In addition, silicon, gallium arsenide, silicon carbide, sapphire, glass, gallium nitride, germanium, etc., which are mentioned as examples of a substrate described later, can also be used as the base material of the indicator of the present invention.

Color-Changing Layer

The color-changing layer varies depending on the treatment to be detected (plasma, ozone, ultraviolet rays, or radical-containing gas). (Hereinafter, the situation where the above treatment is performed is referred to as "under the treatment atmosphere or irradiation area" or simply as "under the treatment.") The color-changing layer for detecting each of the above treatments is described in detail below.

(i) Indicator for Detecting Plasma

The indicator of the present invention includes an indicator for detecting plasma. The indicator for detecting plasma contains a color-changing layer formed by an ink composition whose color changes or disappears by reaction with plasma.

Coloring Agent

The color-changing layer for detecting plasma is suitably formed by an ink composition containing at least one coloring agent (color-changing colorant) selected from the group consisting of anthraquinone colorants, azo colorants, methine colorants, and phthalocyanine colorants. These colorants (dyes) can be used singly or in a combination of two or more.

Anthraquinone colorants may be any colorant that has anthraquinone as a basic skeleton. Known anthraquinone dispersing dyes and the like are also usable. In particular, anthraquinone colorants containing an amino group are preferable. Anthraquinone colorants containing at least one amino group selected from the group consisting of primary amino groups and secondary amino groups are more preferable. In this case, the composition may contain one or more primary amino groups and/or one or more secondary amino groups, and each of the amino groups may be of the same or different type.

Specific examples include 1,4-diaminoanthraquinone (C.I. Disperse Violet 1), 1-amino-4-hydroxy-2-methylaminoanthraquinone (C.I. Disperse Red 4), 1-amino-4-methylaminoanthraquinone (C.I. Disperse Violet 4), 1,4-diamino-2-methoxyanthraquinone (C.I. Disperse Red 11), 1-amino-2-methylanthraquinone (C.I. Disperse Orange 11), 1-amino-4-hydroxyanthraquinone (C.I. Disperse Red 15), 1,4,5,8-tetraminoanthraquinone (C.I. Disperse Blue 1), 1,4-diamino-5-nitroanthraquinone (C.I. Disperse Violet 8), and the like (color index names are in parentheses).

Other usable colorants include those known as C.I. Solvent Blue 14, C.I. Solvent Blue 35, C.I. Solvent Blue 63, C.I. Solvent Violet 13, C.I. Solvent Violet 14, C.I. Solvent Red 52, C.I. Solvent Red 114, C.I. Vat Blue 21, C.I. Vat Blue 30, C.I. Vat Violet 15, C.I. Vat Violet 17, C.I. Vat Red 19, C.I. Vat Red 28, C.I. Acid Blue 23, C.I. Acid Blue 80, C.I. Acid Violet 43, C.I. Acid Violet 48, C.I. Acid Red 81, C.I. Acid Red 83, C.I. Reactive Blue 4, C.I. Reactive Blue 19, C.I. Disperse Blue 7, and the like.

These anthraquinone colorants can be used singly or in a combination of two or more. Among these anthraquinone colorants, C.I. Disperse Blue 7, C.I. Disperse Violet 1, and the like are preferable. In the present invention, detection sensitivity can be controlled by changing the kinds (molecular structures, etc.) of such anthraquinone colorants used.

The azo colorants may be any colorant that has azo-N=N— as a chromophore. Examples of such colorants include monoazo colorants, polyazo colorants, metal complex azo colorants, stilbene azo colorants, thiazole azo colorants, and the like. As indicated by color index names, specific examples of such colorants include C.I. Solvent Red 1, C.I. Solvent Red 3, C.I. Solvent Red 23, C.I. Disperse Red 13, C.I. Disperse Red 52, C.I. Disperse Violet 24, C.I. Disperse Blue 44, C.I. Disperse Red 58, C.I. Disperse Red 88, C.I. Disperse Yellow 23, C.I. Disperse Orange 1, C.I. Disperse Orange 5, C.I. Solvent Red 167:1, and the like. These colorants may be used singly or in a combination of two or more.

The methine colorants may be any colorant that has a methine group. Polymethine colorants, cyanine colorants, and the like are thus also included within the scope of methine colorants in the present invention. These colorants can be appropriately selected from known or commercially available methine colorants. Specific examples include C.I. Basic Red 12, C.I. Basic Red 13, C.I. Basic Red 14, C.I. Basic Red 15, C.I. Basic Red 27, C.I. Basic Red 35, C.I. Basic Red 36, C.I. Basic Red 37, C.I. Basic Red 45, C.I. Basic Red 48, C.I. Basic Yellow 3711, C.I. Basic Yellow 12, C.I. Basic Yellow 13, C.I. Basic Yellow 14, C.I. Basic Yellow 21, C.I. Basic Yellow 22, C.I. Basic Yellow 23, C.I. Basic Yellow 24, C.I. Basic Violet 7, C.I. Basic Violet 15, C.I. Basic Violet 16, C.I. Basic Violet 20, C.I. Basic Violet 21, C.I. Basic Violet 39, C.I. Basic Blue 62, C.I. Basic Blue 63, and the like. These can be used singly or in a combination of two or more.

The phthalocyanine colorants may be any colorant that has a phthalocyanine structure. Examples of such colorants include blue copper phthalocyanine, greenish blue metal-free phthalocyanine, green highly chlorinated phthalocyanine, yellowish green poorly chlorinated phthalocyanine (brominated chlorinated copper phthalocyanine), and the like. Specific examples of such colorants include C.I. Pigment Green 7, C.I. Pigment Blue 15, C.I. Pigment Blue 15:3, C.I. Pigment Blue 15:4, C.I. Pigment Blue 15:6, C.I. Pigment Blue 16, C.I. Pigment Green 36, C.I. Direct Blue 86, C.I. Basic Blue 140, C.I. Solvent Blue 70, and the like. These phthalocyanine colorants can be used singly or in a combination of two or more.

In addition to the above general phthalocyanine colorants mentioned above, other phthalocyanine colorants are also usable. Examples of such colorants include compounds that have as central metal(s) at least one metal selected from the group consisting of zinc, iron, cobalt, nickel, lead, tin, manganese, magnesium, silicon, titanium, vanadium, aluminium, iridium, platinum, and ruthenium, with the central metal(s) being coordinated with phthalocyanine; such compounds in which the central metal(s) are bonded to oxygen or chlorine and are coordinated with phthalocyanine; and the like.

The content of the coloring agent can be appropriately determined according to the kind of coloring agent, the desired hue, etc. The ink composition generally preferably contains a coloring agent in an amount of about 0.05 to 5 wt. %, particularly preferably about 0.1 to 1 wt. %.

In the present invention, colorants and pigments other than the coloring agents mentioned above may also be present. In particular, a colorant component that does not change color under plasma treatment atmosphere ("non-color-changing colorant") may be used. This can enhance the visual recognition effect due to color tone changes from one color to another. The non-color-changing colorant may be a known ink (normal color ink). In this case, the content of the non-color-changing colorant can be appropriately set according to the type of non-color-changing colorant used, etc.

In addition to the above coloring agent, the ink composition for detecting plasma treatment according to the present invention preferably contains at least one member selected from binder resins, nonionic surfactants, cationic surfactants, and extenders.

Binder Resin

The resin binder may be suitably selected according to the type of base material, etc. Known resin components used in ink compositions for writing, printing, etc., can be used. Specific examples of resin binders include maleic resins, ketone resins, alkylphenol resins, rosin-modified resins, polyvinyl butyral, cellulose resins, polyester resins, styrene maleic resins, styrene acrylic acid resins, acrylic resins, and the like. These binder resins can be used singly or in a combination of two or more.

Cellulose resins are particularly preferable for use in the present invention. The use of a cellulose resin can impart excellent fixing properties even when the ink composition contains an extender (e.g., silica), and can efficiently prevent falling, detachment, etc., from the substrate. Efficiently producing cracks on the surface of the coating film of the ink composition can help enhance the sensitivity of the indicator.

In the present invention, the binder resins may be all or partially nitrogen-containing polymers other than the resins mentioned above. The nitrogen-containing polymers function as sensitivity enhancers as well as binders. Specifically, the use of such a sensitivity enhancer can enhance the accuracy (sensitivity) of plasma treatment detection.

Examples of nitrogen-containing polymers include synthetic resins, such as polyamide resins, polyimide resins, polyacrylonitrile resins, amino resins, polyacrylamides, polyvinylpyrrolidones, polyvinylimidazoles, and polyethyleneimines. These resins can be used singly or in a combination of two or more. In particular, polyamide resins are preferably used in the present invention. The type, molecular weight, etc., of polyamide resin are not particularly limited. Known or commercially available polyamide resins can be used. Among these, a polyamide resin that is a reaction product of a dimer of linoleic acid with a diamine or polyamine (a long-chain linear polymer) is suitable for use. Polyamide resins are thermoplastic resins that have a molecular weight of 4,000 to 7,000. Commercially available products can be used as such resins.

The content of the binder resin can be appropriately determined according to the types of binder resin and coloring agent used, etc. The amount of the binder in the ink composition is generally preferably about 50 wt. % or less, and particularly preferably 5 to 35 wt. %. When the nitrogen-containing polymer is used as a binder resin, the amount of the nitrogen-containing polymer in the ink composition is preferably about 0.1 to 50 wt. %, and particularly preferably 1 to 20 wt. %.

Nonionic Surfactant

In the ink composition of the present invention, the nonionic surfactant functions as a color change accelerator. Using the nonionic surfactant with a coloring agent can provide more excellent detection sensitivity.

The nonionic surfactant is at least one of the surfactants represented by formulae (I) to (V).

The nonionic surfactants represented by formula (I)

$$R_1\text{—}X\text{-}(AO)_n\text{—}R_2 \quad (I)$$

(wherein $R_1$ and $R_2$ are each independently hydrogen or a straight-chain or branched aliphatic hydrocarbon group having 1 to 30 carbon atoms; X is oxygen or an ester bond; AO is a repeating unit derived from an alkylene oxide; and n is an integer of 1 to 200) are alkylene glycol derivatives.

The nonionic surfactants represented by formula (II)

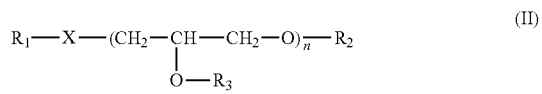

(wherein $R_1$, $R_2$, and $R_3$ are each independently hydrogen or a straight-chain or branched aliphatic hydrocarbon group having 1 to 30 carbon atoms; X is oxygen or an ester bond; and n is an integer of 1 to 200) are polyglycerin derivatives.

In formula (I), examples of AO (monomers) include ethylene oxide, propylene oxide, 1,2-butylene oxide, 2,3-butylene oxide, tetrahydrofuran, styrene oxide, and the like. The form of polymerization of AO may be a homopolymer, or a block copolymer or a random copolymer of two or more kinds of AOs. In formulae (I) and (II), "having 1 to 30 carbon atoms" refers to preferably having 1 to 22 carbon atoms, and more preferably having 10 to 18 carbon atoms. X is preferably oxygen, and n is preferably an integer of 1 to 100.

Specific examples of nonionic surfactants that can be represented by the above formula (I) or (II) include polyethylene glycols (for example, the commercially available product PEG2000 produced by Sanyo Chemical Industries, Ltd.), glycerol, polyethylene glycol-polypropylene glycol copolymers (for example, the commercially available product Epan 710 produced by Dai-Ichi Kogyo Seiyaku Co., Ltd.), and the like.

In the above, polymers wherein at least one of $R_1$ and $R_2$ is substituted with a straight-chain or branched aliphatic hydrocarbon group having 1 to 30 carbon atoms are also preferable.

Specific examples include polyoxyethylene (hereinafter "POE") lauryl ethers (for example, the commercially available product Emulgen 109P), POE cetyl ethers (for example, the commercially available product Emulgen 220), POE oleyl ethers (for example, the commercially available product Emulgen 404), POE stearyl ethers (for example, the commercially available product Emulgen 306), and POE alkyl ether (for example, the commercially available product Emulgen LS-110) (all produced by Kao Corp.); POE tridecyl ethers (for example, the commercially available product Fine Serve TD-150) and polyethylene glycol monostearates (for example, the commercially available product S-400A) (both produced by Aoki Oil Industrial Co., Ltd.); polyethylene glycol monooleate (for example, the commercially available product Nonion O-4), tetramethylene glycol derivatives (for example, the commercially available product polyserine DC-1100), polybutylene glycol derivatives (for example, the commercially available product Uniol PB-500), and alkylene glycol derivatives (for example, the commercially available product Unilube 50 MB-5) (all produced by NOF Corporation); POE(20) octyldodecyl ether (for example, the commercially available product Emma Rex OD-20) and POE(25) octyldodecyl ether (for example, the commercially available product Emma Rex OD-25) (both produced by Japan Emulsion Co. Ltd.); and the like.

The nonionic surfactants represented by formulae (III) and (IV)

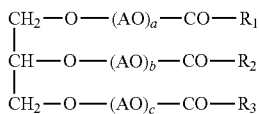

(wherein $R_1$, $R_2$, and $R_3$ are each independently hydrogen or a straight-chain or branched aliphatic hydrocarbon group having 1 to 30 carbon atoms; AO is a repeating unit derived from alkylene oxide; and the sum of a, b, and c is an integer of 3 to 200) are alkylene glycol glyceryl derivatives.

In both of the above formulae, examples of AO (monomer) include ethylene oxide, propylene oxide, 1,2-butylene oxide, 2,3-butylene oxide, tetrahydrofuran, styrene oxide, and the like. The form of polymerization of AO may be a homopolymer, or a block copolymer or a random copolymer of two or more kinds of AO. In both of the above formulae, "having 1 to 30 carbon atoms" refers to preferably having 1 to 22 carbon atoms, and more preferably having 10 to 18 carbon atoms, and the sum of a, b, and c is preferably an integer of 3 to 50.

Examples of nonionic surfactants represented by formula (III) include compounds wherein $R_1$ is an isostearic acid residue, $R_2$ and $R_3$ are hydrogen, and AO (monomer) is ethylene oxide. Specific examples include POE glyceryl isostearates (for example, the commercially available product Uniox GM-30IS produced by NOF Corporation).

Examples of nonionic surfactants represented by formula (IV) include compounds wherein $R_1$ to $R_3$ are isostearic acid residues, and AD (monomer) is ethylene oxide. Specific examples include POE glyceryl triisostearate (for example, the commercially available product Uniox GT-30IS produced by NOF Corporation).

The nonionic surfactants represented by formula (V)

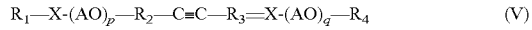

(wherein $R_1$, $R_2$, $R_3$, and $R_4$ are independently hydrogen or a straight-chain or branched aliphatic hydrocarbon group having 1 to 30 carbon atoms, X is oxygen or an ester bond, AO is a repeating unit derived from alkylene oxide, and the sum of p and q is an integer of 0 to 20) are acetylene glycol derivatives.

In formula (V), examples of AO (monomers) include ethylene oxide, propylene oxide, 1,2-butylene oxide, 2,3-butylene oxide, tetrahydrofuran, styrene oxide, and the like. The polymerization form of AO includes a homopolymer, or a block copolymer or a random copolymer of two or more kinds of AOs. In formulae (I) and (II), "having 1 to 30 carbon atoms" refers to preferably having 1 to 22 carbon atoms, X is preferably oxygen, and the sum of p and q is preferably an integer of 0 to 10.

Examples of nonionic surfactants represented by formula (V) include compounds wherein $R_1$ and $R_4$ are hydrogen, $R_2$ and $R_3$ are $>C(CH_3)$ (i-$C_4H_9$), X is oxygen, and p+q=0. Specific examples include 2,4,7,9-tetramethyl-5-decyn-4,7-diol (for example, the commercially available product Surfynol 104H produced by Air Products Japan, Inc.).

The nonionic surfactants represented by formulae (I) to (V) can be used singly or in a combination of two or more.

The content of the nonionic surfactant can be suitably determined according to the types of nonionic surfactant and coloring agent used, etc. In consideration of the preservability in the composition and color-change-accelerating effect, the content of the nonionic surfactant in the ink composition is generally preferably about 0.2 to 10 wt. %, and particularly preferably 0.5 to 5 wt. %.

Cationic Surfactant

The cationic surfactant is not particularly limited; however, at least one member selected from tetraalkylammnonium salts, isoquinolinium salts, imidazolinium salts, and pyridinium salts is particularly preferably used. Commercially available cationic surfactants can also be used. The combined use of a cationic surfactant with a coloring agent mentioned above can provide more excellent detection sensitivity. The above cationic surfactants can be used singly or in a combination of two or more.

Among tetraalkylammonium salts, alkyl trimethyl ammnonium salts, dialkyl dimethyl ammonium salts, etc., are preferred. Specific examples include coconut alkyl trimethyl ammonium chloride, beef tallow alkyl trimethyl ammonium chloride, behenyl trimethyl ammonium chloride, myristyl trimethyl ammonium chloride, tetramethyl ammonium chloride, tetrabutyl ammonium chloride, tetrapropyl ammonium chloride, tetramethyl ammonium bromide, tetrabutyl ammonium bromide, tetrapropyl ammonium bromide, trimethyl-2-hydroxyethyl ammonium chloride, cetyltrimethyl ammnonium chloride, lauryl trimethyl ammnonium chloride, stearyl trimethyl ammonium chloride, dioctyl dimethyl ammonium chloride, distearyl dimethyl ammonium chloride, alkyl benzyl dimethyl ammonium chloride, and the like. Particularly preferred are behenyl trimethyl ammonium chloride, lauryl trimethylammonium chloride, etc.

Examples of isoquinolinium salts include lauryl isoquinolinium bromide, cetyl isoquinolinium bromide, cetyl isoquinolinium chloride, lauryl isoquinolinium chloride, and the like. Particularly preferred among these is lauryl isoquinolinium bromide.

Examples of imidazolinium salts include 1-hydroxyethyl-2-oleylimidazolinium chloride, 2-chloro-1,3-dimethylimidazolinium chloride, and the like. Particularly preferred among these is 2-chloro-1,3-dimethylimidazolinium chloride.

Examples of pyridinium salts include pyridinium chloride, 1-ethylpyridinium bromide, hexadecylpyridinium chloride, cetylpyridinium chloride, 1-butylpyridinium chloride, N-n-butylpyridinium chloride, hexadecylpyridinium bromide, N-hexadecylpyridinium bromide, 1-dodecylpyridinium chloride, 3-methylhexylpyridinium chloride, 4-methylhexylpyridinium chloride, 3-methyloctylpyridinium chloride, 2-chloro-1-methylpyridinium iodide, 3,4-dimethylbutylpyridinium chloride, pyridinium-n-hexadecyl chloride-hydrate, N-(cyanomethyl)pyridinium chloride, N-acetonylpyridinium bromide, 1-(aminoformylmethyl) pyridinium chloride, 2-amidinopyridinium chloride, 2-aminopyridinium chloride, N-aminopyridinium iodide, 1-aminopyridinium iodide, 1-acetonylpyridinium chloride, N-acetonylpyridinium bromide, and the like. Particularly preferred among these is hexadecylpyridinium chloride.

The content of the cationic surfactant can be suitably determined according to the type of surfactant, the type of coloring agent used, etc. In general, the content of the cationic surfactant in the ink composition is preferably about 0.2 to 10 wt. %, and particularly preferably 0.5 to 5 wt. %.

Extender

Any extender can be used, and examples of extenders include bentonite, activated clay, aluminum oxide, silica, silica gel, and like inorganic materials. Materials known as extender pigments can also be used. Among these, at least one member selected from the group consisting of silica, silica gel, and alumina is preferable, and silica is particularly preferable. When silica or the like is used, cracks can be effectively produced particularly on the surface of the color-changing layer. As a result, the detection sensitivity of the indicator can be further increased. The above extenders can be used singly or in a combination of two or more.

The content of the extender can be suitably determined according to the types of extender and coloring agent used, etc. In general, the content of the extender in the ink composition is preferably about 1 to 30 wt. %, and particularly preferably 2 to 20 wt. %.

Other Additives

If required, the ink composition of the present invention may contain components used in known inks, such as solvents, leveling agents, antifoaming agents, UV absorbers, and surface conditioners.

Solvents that can be used in the present invention may be any solvent that is used in ink compositions for printing, writing, etc. Usable solvents are various solvents such as alcohol-based, polyhydric alcohol-based, ester-based, ether-based, ketone-based, hydrocarbon-based, and glycol ether-based solvents. The solvent to be used can be suitably selected in consideration of the solubility of the colorant and binder resin used, etc. The above solvents can be used singly or in a combination of two or more.

The content of the solvent can be suitably determined according to the types of solvent and coloring agent used, etc. In general, the content of the solvent in the ink composition is preferably about 40 to 95 wt. %, and particularly preferably 60 to 90 wt. %.

The components of the ink composition of the present invention can be added all at once or sequentially and mixed uniformly by using a known stirrer, such as a homogenizer or a dissolver. For example, first the coloring agent mentioned above and at least one member selected from the group consisting of binder resins, cationic surfactants, and extenders (other additives as required) may be sequentially added to a solvent, and the resultant mixture may be mixed and stirred using a stirrer.

Method for Forming Color-Changing Layer

The color-changing layer can be formed using the above ink composition according to known printing methods, such as spin coating, slit coating, sol-gel coating, spray coating, silk screen printing, gravure printing, offset printing, relief printing, and flexographic printing; or according to known coating methods. The color-changing layer can also be formed by various methods other than the above printing methods. For example, the color-changing layer can be formed by immersing a base material into an ink composition. Such methods are particularly preferable for materials into which ink permeates, such as nonwoven fabrics.

The color-changing layer preferably has cracks on the surface. Specifically, the color-changing layer preferably has open pores formed on the surface of the color-changing layer and is porous. With this structure, the detection sensitivity of the plasma treatment indicator can be further enhanced. In this case, the desired color change effect can be obtained even when the color-changing layer is disposed in the plasma treatment detection indicator. Cracks can be effectively formed by using a cellulose resin as a binder resin for the ink composition of the present invention. Specifically, use of a cellulose resin enables the formation of cracks as mentioned above, while maintaining good fixing properties.

Plasma

Plasma is not particularly limited, and any plasma generated by a plasma generation gas can be used. Preferable among such plasmas is plasma generated by at least one plasma generation gas selected from the group consisting of oxygen, nitrogen, hydrogen, chlorine, argon, silane, ammonia, sulfur bromide, water vapor, nitrous oxide, tetraethoxysilane, carbon tetrafluoride, trifluoromethane, carbon tetrachloride, silicon tetrachloride, sulfur hexafluoride, titanium tetrachloride, dichlorosilane, trimethylgallium, trimethylindium, and trimethylaluminum.

Plasma is useful as an indicator in a plasma treatment apparatus (an apparatus that generates plasma by application of AC power, DC power, pulse power, high-frequency power, microwave power, etc., in an atmosphere containing a plasma generation gas so as to perform plasma treatment).

(ii) Indicator for Detecting Ozone

The indicator of the present invention includes an indicator for detecting ozone. The indicator for detecting ozone contains a color-changing layer formed by an ink composition whose color changes or disappears by reaction with ozone.

Coloring Agent

The color-changing layer for detecting ozone is suitably formed by an ink composition containing at least one coloring agent (color-changing colorant) selected from the group consisting of oxazine colorants, azo colorants, methine colorants, and anthraquinone colorants. These colorants can be used singly or in a combination of two or more.

Oxazine colorants are not particularly limited, as long as they have at least one oxazine ring of the following formulae (I) to (III). Examples include monooxazine colorants having one oxazine ring, dioxazine colorants having two oxazine rings, etc.

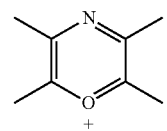

I

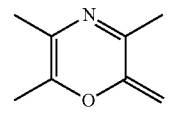

II

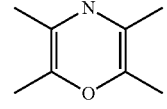

III

Moreover, in the present invention, a basic colorant having at least one substituted or unsubstituted amino group, a chrome-mordanting colorant further having OH, COOH, etc., as a substituent, or the like can be used as an auxochrome.

These oxazine colorants can be used singly or in a combination of two or more. Known or commercially available oxazine colorants can also be used. More specifically, in terms of the dye number (colorant number), preferably used oxazine colorants are C.I. Basic Blue 3, C.I. Basic Blue 12, C.I. Basic Blue 6, C.I. Basic Blue 10, C.I. Basic Blue 96, and the like. In particular, C.I. Basic Blue 3, etc., are preferred.

Usable anthraquinone colorants are the same anthraquinone colorants mentioned in the "(i) Indicator for detecting plasma" section. Preferable anthraquinone colorants are also the same as those mentioned in the "(i) Indicator for detecting plasma" section. The anthraquinone colorants can be used singly or in a combination of two or more.

Usable azo colorants are the same azo colorants mentioned in the "(i) Indicator for detecting plasma" section. The azo colorants can be used singly or in a combination of two or more.

Usable methine colorants are the same methine colorants mentioned in the "(i) Indicator for detecting plasma" section. The methine colorants can be used singly or in a combination of two or more.

The content of such a colorant depends on the type of colorant used, the desired color-changing properties (detection accuracy), etc. In general, the content of the colorant in the ink composition is preferably 0.1 to 5 wt. %, and particularly preferably 1 to 4 wt. %.

Cationic Surfactant

The indicator for detecting ozone preferably contains a cationic surfactant in the ink composition. Preferable cationic surfactants are tetraalkylammonium salt-type cationic surfactants. Tetraalkylammonium salt-type cationic surfactants are not particularly limited, and usable cationic surfactants are the same tetraalkylamnonium salts mentioned in the "(i) Indicator for detecting plasma" section. Preferable tetraalkylamnonium salts are also the same as those mentioned in the "(i) Indicator for detecting plasma" section. These can be used singly or in a combination of two or more. In the present invention, the use of such cationic surfactants can provide more excellent color change effects.

The content of the cationic surfactant depends on the type of cationic surfactant used, the desired color-changing properties (detection accuracy), etc. In general, the content of the cationic surfactant in the ink composition is preferably 0.01 to 8 wt. %, and particularly preferably 0.1 to 4 wt. %. The ozone detection sensitivity can be controlled more effectively by setting the content of the cationic surfactant within the above range.

Binder Resin, Extender, and Other Additives

The ink composition for detecting ozone treatment according to the present invention may further contain, as required, components used in known ink compositions, such as binder resins, extenders, solvents, and colorant components whose color does not change by ozone.

The binder resin may be suitably selected according to the type of base material, etc. For example, known resin components used in ink compositions for writing, printing, etc., can be used as they are. Specific examples include maleic resins, amide resins, ketone resins, alkylphenol resins, rosin-modified resins, polyvinyl butyral, polyvinylpyrrolidone, cellulose resins, and the like. These binder resins can be used singly or in a combination of two or more.

In general, the content of the binder resin in the ink composition is preferably 1 to 25 wt. %, and particularly preferably 1 to 20 wt. %. More excellent coating films (printing layers) can be formed by setting the content of the binder resin within the above range.

Usable extenders are the same extenders mentioned in the "(i) Indicator for detecting plasma" section. Preferable extenders are also the same as those mentioned in the "(i) Indicator for detecting plasma" section. These extenders can be used singly or in a combination of two or more.

In general, the content of the extender in the ink composition is preferably 1 to 20 wt. %, and particularly preferably 1 to 10 wt. %. Smoother coating surfaces (printing surfaces) can be obtained by setting the content of the extender within the above range.

Usable solvents are the same solvents mentioned in the "(i) Indicator for detecting plasma" section. The content of the solvent is also the same as the content of the solvent mentioned in the "(i) Indicator for detecting plasma" section. These solvents can be used singly or in a combination of two or more.

Usable colorant components whose color does not change by ozone include any colorant components whose color does not change in an ozone atmosphere. Usable colorant components whose color does not change in an ozone atmosphere include known inks, such as normal color ink. For example, water-based inks, oil-based inks, solventless inks, and the like can be used. For printing, known relief printing inks, gravure inks, screen inks, offset inks, etc., can be suitably used according to the printing method. These inks may be used singly as they are, or two or more of these inks may be mixed to create a color. Moreover, the ink of a non-color-changing layer, described later, may contain components mixed in known ink compositions (e.g., binder resins, extenders, and solvents).

In general, the content of the colorant component in the ink composition is preferably 0.01 to 10 wt. %, and particularly preferably 0.1 to 4 wt. %.

The components of the ink composition for detecting ozone treatment according to the present invention may be mixed by the same method mentioned in the "(i) Indicator for detecting plasma" section.

Method for Forming Color-Changing Layer

The indicator for detecting ozone can be formed by the same method for forming a color-changing layer mentioned in the "(i) Indicator for detecting plasma" section.

Ozone

The indicator for detecting ozone according to the present invention can change in color even in a high-concentration region having a CT value (CT value=concentration×exposure time) of 300 ppm·min or more, particularly 500 ppm·min or more, preferably 1,000 ppm·min or more, and more preferably 1,000 ppm·min or more. The upper limit of the CT value is not limited, but is generally about 100,000 ppm·min. The same effect can be exhibited even when the color-changing layer of the indicator for detecting ozone is placed so as to be directly exposed to an ozone atmosphere. That is, the indicator for detecting ozone according to the present invention may not have a protective layer, etc., on the color-changing layer.

Moreover, in an ozone treatment atmosphere containing water vapor, the indicator for detecting ozone can accurately detect ozone generally in a humidity range of 10% or more, and particularly under high humidity in a humidity range of 90% or more. Accordingly, the indicator for detecting ozone can be suitably used, for example, in a device for cleaning an object to be treated with ozone water, to detect ozone gas generated from the ozone water. The ozone gas is highly concentrated and contains a large amount of water vapor. Even in such an atmosphere, the indicator for detecting ozone according to the present invention can more accurately detect the presence of ozone, and can further detect ozone concentration, ozone exposure time, or CT values.

(iii) Indicator for Detecting Ultraviolet-Rays

The indicator of the present invention includes an indicator for detecting ultraviolet rays. The indicator for detecting ultraviolet rays contains a color-changing layer formed by an ink composition whose color changes or disappears by reaction with ultraviolet rays.

Coloring Agent and Compound

The color-changing layer for detecting ultraviolet rays is suitably formed by an ink composition containing the following coloring agent (color-changing colorant) (a) and compound (b):

(a) at least one colorant selected from the group consisting of azo colorants, anthraquinone colorants, indigo colorants, triphenylmethane colorants, diphenylmethane colorants, triphenylamine colorants, phthalocyanine colorants, and cyanine colorants; and (b) at least one compound selected from the group consisting of acetophenone-type compounds, benzophenone-type compounds, Michler's ketone-type compounds, benzyl-type compounds, benzoin-type compounds, benzoin ether-type compounds, benzyl dimethyl ketal-type compounds, benzoin benzoate-type compounds, α-acetyloxy ester-type compounds, tetramethylthiuram monosulfide-type compounds, thioxanthone-type compounds, and acylphosphine oxide-type compounds. Compound (b) gives a change to the coloring mechanism of the colorant by ultraviolet irradiation, and includes both of the following compounds:

[1] a compound that upon ultraviolet irradiation is transformed to a compound that itself gives a change to the coloring mechanism of the colorant; and

[2] a compound that upon ultraviolet irradiation generates free radicals giving a change to the coloring mechanism of the colorant.

Of these compounds, compound [2] is preferable, and compounds having an absorption maximum at a wavelength of about 150 to 450 nm (even more preferably 200 to 400 nm) are more preferable. The above colorants can be used singly or in a combination of two or more, and the above compounds can be used singly or in a combination of two or more.

When the above compound is a benzophenone-type compound, a Michler's ketone-type compound, a benzyl-type compound, a thioxanthone-type compound, or the like, it is preferable to use it in combination with an amine-based reaction accelerator (amine-based radical accelerator), described later. The amount of the amine-based reaction accelerator can be suitably determined according to the above compound, colorant, etc.

The content of the above compound can be determined according to the type of colorant used, etc.; however, in order to obtain color change effects sufficient for visual observation, and to prevent any defects in the solubility in solvents, etc., the content of the compound is generally about 0.1 to 20 mol, and preferably 0.5 to 15 mol, per mole of the colorant.

Examples of preferred combinations of the above compound and colorant are as follows:

(1) a combination of an anthraquinone colorant with a benzoin ether-type compound, a benzyl dimethyl ketal-type compound, or an acylphosphine oxide-type compound;

(2) a combination of a disazo colorant with a benzoin ether-type compound or an acylphosphine oxide-type compound;

(3) a combination of a phthalocyanine colorant with a benzoin ether-type compound or an acylphosphine oxide-type compound;

(4) a combination of a cyanine colorant with a benzophenone-type compound; and (5) a combination of an azo colorant with a benzophenone-type compound or an acylphosphine oxide-type compound.

The amount of the colorant in the ink composition may be suitably determined according to the type of the above compound, the form of the product, etc. For example, when the ink composition of the present invention is a liquid ink, the amount of the colorant is generally about 0.01 to 20 wt. %, and preferably 0.1 to 10 wt. %, so as to sufficiently dissolve the colorant in a solvent, and not to reduce the color difference before and after color change.

Binder Resin, Extender, and Other Additives

In addition to the above components, the ink composition for detecting ultraviolet treatment according to the present invention may contain, as required, known additives within a range in which the color change effects are not impaired. Examples of additives include binder resins, inorganic fillers, various solvents, reaction accelerators, reaction retardants, etc.

Examples of binder resins include natural resins, such as rosin and rosin esters; phenolic resins, urea resins, melamine resins, vinyl-based resins (vinyl chloride-vinyl acetate-based copolymer, polystyrene, etc.), polyester-based resins (maleic acid polymerized resin, alkyd resin, etc.), and the like. These binder resins can be used singly or in a combination of two or more.

Examples of inorganic fillers include silica powder, titanium oxide powder, calcium carbonate powder, alumina silicate powder, and the like. These inorganic fillers can be used singly or in a combination of two or more.

Examples of solvents include hydrocarbon-based solvents, such as toluene, xylene, benzene, and tetralin; alcohol-based solvents, such as ethyl alcohol and butyl alcohol; ether-based solvents, such as ethyl cellosolve and ethyl ether; halogenated hydrocarbons; phenols; ketones; and the like. These solvents can be used singly or in a combination of two or more.

Examples of reaction accelerators include known amine-based radical accelerators; zinc compounds, such as zinc nitrate and zinc fatty acid soap; lead compounds, such as lead carbonate and lead phthalate; cadmium compounds, such as cadmium laurate and cadmium fatty acid soap; urea; borax; ethanolamine; and the like. These reaction accelerators can be used singly or in a combination of two or more.

Examples of reaction retardants include organic acids, such as maleic acid and fumaric acid; halogenated organic acids, such as stearoyl chloride; anhydrous organic acids, such as phthalic anhydride; polyhydroxylated compounds, such as hydroquinone and naphthalenediol; nitrogen-containing compounds, such as oxime and aliphatic amine; sulfur compounds; ketones; aldehydes; phosphates; and the like. These reaction retardants can be used singly or in a combination of two or more.

The ink composition of the present invention is obtained by mixing the above compound and colorant, and optionally other additives, by a known method. Moreover, the ink composition can be mixed with a thermoplastic material in a thermally molten state, without using a solvent, and formed into a desired shape. In this case, usable thermoplastic materials include aliphatic ester wax, polyethylene glycol, and plastics such as vinyl resin, styrene resin, and acrylic resin. Furthermore, the ink composition can also be supported by a porous material, such as silica particles.

Method for Forming Color-Changing Layer

The indicator for detecting ultraviolet rays can be formed by the same method for forming a color-changing layer mentioned in the "(i) Indicator for detecting plasma" section.

Ultraviolet Rays

The indicator for detecting ultraviolet rays according to the present invention uses a color change mechanism using ultraviolet irradiation. Specifically, [1] upon ultraviolet irradiation, compound (b) above is transformed to a compound that itself gives a change to the coloring mechanism of the colorant, and the resulting compound changes or removes the color of the colorant; or [2] upon ultraviolet irradiation, compound (b) above generates free radicals giving a change to the coloring mechanism of the colorant, and the resulting free radicals change or remove the color of the colorant.

The ultraviolet rays used in the present invention refer to electromagnetic waves with a wavelength of about 1 to 400 nm, and include near ultraviolet rays, far ultraviolet rays, vacuum ultraviolet rays, extreme ultraviolet rays, and super ultraviolet rays.

(iv) Indicator for Detecting Radical-Containing Gas

The indicator of the present invention includes an indicator for detecting radical-containing gas. The indicator for detecting radical-containing gas contains a color-changing layer formed by an ink composition whose color changes or disappears by reaction with radical-containing gas.

The color-changing layer for detecting radical-containing gas is suitably formed by an ink composition containing at least one coloring agent (color-changing colorant) selected from the group consisting of anthraquinone colorants, azo colorants, and triarylmethane colorants.

Coloring Agent

Usable anthraquinone colorants are the same anthraquinone colorants mentioned in the "(i) Indicator for detecting plasma" section. Preferable anthraquinone colorants are also the same as those mentioned in the "(i) Indicator for detecting plasma" section. The anthraquinone colorants can be used singly or in a combination of two or more.

Usable azo colorants are the same azo colorants mentioned in the "(i) Indicator for detecting plasma" section. The azo colorants can be used singly or in a combination of two or more.

Triarylmethane colorants are not limited, and known or commercially available colorants can be used. Examples include C.I. Basic Blue 1, C.I. Basic Blue 26, C.I. Basic Blue 5, C.I. Basic Blue 8, C.I. Basic Green 1, C.I. Basic Red 9, C.I. Basic Violet 12, C.I. Basic Violet 14, C.I. Basic Violet 3, C.I. Solvent Green 15, C.I. Solvent Violet 8, and the like. These can be used singly or in a combination of two or more. Of these triarylmethane colorants, C.I. Solvent Violet 8, C.I. Basic Green 1, C.I. Basic Red 9, C.I. Basic Blue 1, etc., can be preferably used.

The content of such a colorant can be suitably determined according to the type of the colorant, the desired hue, etc. In general, the content of the colorant in the ink composition is preferably about 0.05 to 5 wt. %, and particularly preferably 0.1 to 1 wt. %.

In the present invention, colorants and pigments other than the coloring agents mentioned above may also be present. In particular, a colorant component that does not change color under radical-containing gas treatment atmosphere ("non-color-changing colorant") may be used. This can enhance the visual recognition effect due to color tone changes from one color to another. The non-color-changing colorant may be a known ink (normal color ink). In this case, the content of the non-color-changing colorant can be appropriately set according to the type of non-color-changing colorant used, etc.

Cationic Surfactant, Binder Resin, Extender, and Other Additives

The ink composition for detecting radical-containing gas treatment according to the present invention preferably contains a cationic surfactant. Usable cationic surfactants are the same cationic surfactants mentioned in the "(i) Indicator for detecting plasma" section. Preferable cationic surfactants and the content of the cationic surfactant are also the same as those mentioned in the "(i) Indicator for detecting plasma" section. The cationic surfactants can be used singly or in a combination of two or more.

The ink composition of the present invention may contain, as required, components used in known inks, such as binder resins, extenders, solvents, leveling agents, antifoaming agents, UV absorbers, and surface conditioners. The method for mixing these components is the same as that mentioned in the "(i) Indicator for detecting plasma" section.

Usable binder resins are the same binder resins mentioned in the "(i) Indicator for detecting plasma" section. Polyamide resins can also be used. Preferable binder resins and the content of the binder resin are also the same as those mentioned in the "(i) Indicator for detecting plasma" section. The binder resins can be used singly or in a combination of two or more.

Usable extenders are the same extenders mentioned in the "(i) Indicator for detecting plasma" section. Preferable extenders and the content of the extender are also the same as those mentioned in the "(i) Indicator for detecting plasma" section. The extenders can be used singly or in a combination of two or more.

Usable solvents are the same solvents mentioned in the "(i) Indicator for detecting plasma" section. The content of the solvent is also the same as that mentioned in the "(i) Indicator for detecting plasma" section. The solvents can be used singly or in a combination of two or more.

The components of the ink composition for detecting radical-containing gas treatment according to the present invention may be mixed by the same method mentioned in the "(i) Indicator for detecting plasma" section.

Method for Forming Color-Changing Layer

The indicator for detecting radical-containing gas can be formed by the same method for forming a color-changing layer mentioned in the "(i) Indicator for detecting plasma" section.

Radical-Containing Gas

In the indicator for detecting radical-containing gas according to the present invention, the above colorant in the present invention reacts with radical active species to cause color change upon exposure to a radical-containing gas atmosphere.

The radical-containing gas used in the present invention is preferably radical-containing gas that contains hydrogen as a raw material. When a substrate is irradiated with radical-containing gas containing hydrogen as a raw material, the natural oxidation film on the surface of the substrate can be cleaned at a lower temperature (e.g., 400° C. or less), compared with thermal decomposition cleaning. It is thus beneficial to use the indicator for detecting radical-containing gas containing hydrogen as a raw material in an electronic device manufacturing apparatus using the radical-containing gas containing hydrogen as a raw material.

The radical-containing gas containing hydrogen as a raw material can be generated, for example, by passing hydrogen through a fine Ta tube heated to 2,100 K by electron-beam bombardment. In an environment in which the radical-containing gas containing hydrogen as a raw material is used, it is preferable to maintain the degree of vacuum at about $1.0 \times 10^{-4}$ to $1.0 \times 10^{-6}$ Torr by controlling the hydrogen flow.

Form of Ink Composition

The form in which the ink composition of the present invention is used is not particularly limited. For example, the ink composition can be used in various forms, such as liquid (solution, dispersion, etc.), film, sheet, aerosol, powder, granules, or microcapsules. Specifically, a product obtained by dissolving or dispersing the ink composition of the present invention in a suitable vehicle can be used as a coating composition, printing ink, aerosol, etc. When the ink composition is used as a film or sheet, it may be applied or printed on various base materials.

Non-Color-Changing Layer

In the present invention, a non-color-changing layer whose color does not change or disappear by reaction with at least one member selected from the group consisting of plasma, ozone, ultraviolet rays, and radical-containing gas may be further formed on the base material and/or on the color-changing layer. The non-color-changing layer can typically be formed by using a commercially available normal color ink. For example, water-based inks, oil-based inks, solventless inks, and the like can be used in the indicator for detecting plasma, the indicator for detecting radical-containing gas, etc. The ink for use in the formation of the non-color-changing layer may optionally contain components used in known inks, such as resin binders, extenders, and solvents.

The non-color-changing layer may be formed in the same manner as the formation of the color-changing layer. For example, the non-color-changing layer can be formed by using a normal color ink according to a known printing method, such as silk screen printing, gravure printing, offset printing, relief printing, or flexographic printing. The order of printing the color-changing layer and the non-color-changing layer is not particularly limited, and may be suitably selected according to the design to be printed, etc.

Layer Structure

The indicator of the present invention may comprise one color-changing layer and one non-color-changing layer, or two or more color-changing layers and two or more non-color-changing layers. Color-changing layers may be laminated together, or non-color-changing layers may be laminated together. In this case, compositions of the color-changing layers may be the same or different. Compositions of the non-color-changing layers may also be the same or different.

Further, the color-changing layer and the non-color-changing layer may be formed partially or entirely on the base material or on the layers. In these cases, in particular, in order for the color-changing layer to reliably change color, it is sufficient that color-changing layer(s) and non-color-changing layer(s) be formed in such a manner that at least one color-changing layer is partially or entirely exposed to each of the above treatments.

In the present invention, the color-changing layer and non-color-changing layer may be freely combined insofar as completion of each of the above treatments can be confirmed. For example, the color-changing layer and non-color-changing layer can be formed in such a manner that the color difference between them can be recognized only after the color of the color-changing layer changes, or in such a manner that the color difference between them disappears only after the color of the color-changing layer changes. In the present invention, it is particularly preferable to form the color-changing layer and non-color-changing layer in such a manner that the color difference between them can be recognized only after the color of the color-changing layer changes.

To enable the color difference to be recognized, for example, the color-changing layer and non-color-changing layer may be formed in such a manner that at least one of characters, patterns, and symbols appear only after the color of the color-changing layer changes. In the present invention, characters, patterns, and symbols include any information that notifies color change. Such characters and the like may be suitably designed according to the intended use, etc.

The color of the non-color-changing layer and the color of the color-changing layer before color change may be different from each other. For example, the color-changing layer and the non-color-changing layer may have substantially the same color, and the color difference (contrast) between the color-changing layer and the non-color-changing layer may be made recognizable only after color change occurs.

According to the indicator of the present invention, the color-changing layer and the non-color-changing layer can be formed in such a manner that the color-changing layer and the non-color-changing layer do not overlap. This can save the amount of ink used.

In the present invention, another color-changing layer or non-color-changing layer may be further formed on either the color-changing layer or the non-color-changing layer, or on both. For example, when a color-changing layer having a different design is formed on a layer comprising a color-changing layer and a non-color-changing layer formed in such a manner that the color-changing layer and the non-color-changing layer are not overlapped (referred to as "a color changing/non-color-changing layer"), the boundary between the color-changing layer and the non-color-changing layer in the color changing/non-color-changing layer cannot be substantially recognized. Thus, a more excellent design can be attained.

In the present invention, preferred embodiments of the layer structure include:

(i) an indicator in which a color-changing layer is formed adjacent to at least one main surface of a base material; and (ii) an indicator in which a non-color-changing layer and a color-changing layer are sequentially formed on a base material, the non-color-changing layer is formed adjacent to the main surface of the base material, and the color-changing layer is formed adjacent to the main surface of the non-color-changing layer.

In embodiment (i), an indicator in which a non-color-changing layer is formed adjacent to the main surface of a color-changing layer is also preferred.

Shape

The shape of the indicator of the present invention is the same as the shape of a substrate. The indicator of the present invention can thereby serve as a so-called dummy substrate and easily detect whether the above treatment is uniformly performed on the entire substrate.

The phrase "the shape of the indicator is the same as the shape of a substrate used in an electronic device manufacturing apparatus" as used herein includes the following causes:

(i) the shape of the indicator is completely the same as the shape of the substrate used in the electronic device manufacturing apparatus; and (ii) the shape of the indicator is substantially the same as the shape of the substrate used in the electronic device manufacturing apparatus so that the indicator can be placed (inserted) in the installation place of the substrate in each electronic device manufacturing apparatus that performs the above treatment.

For example, in case (ii), the phrase "substantially the same" includes the following: the difference between the length of the main surface of a substrate (or the diameter of a substrate having a circular main surface, or the vertical and horizontal length of a substrate having a square, rectangle or the like main surface) and the length of the main surface of the indicator of the present invention is ±5.0 mm or less, and the difference between the thickness of the substrate and the thickness of the indicator of the present invention is about ±1000 μm or less.

The indicator of the present invention is preferably used in an electronic device manufacturing apparatus that performs at least one process selected from the group consisting of oxidation, nitriding, film formation, impurity addition, cleaning, and etching, described later, on a substrate.

Designing and/or Managing Method of the Present Invention

The method of the present invention is a method for designing and/or managing an electronic device manufacturing apparatus, and is characterized in that:

(1) the designing and/or managing method comprises the step of placing an indicator that detects at least one member selected from the group consisting of plasma, ozone, ultraviolet rays, and radical-containing gas under treatment with at least one member selected from the group consisting of plasma, ozone, ultraviolet rays, and radical-containing gas;

(2) the indicator has a shape that is the same as that of a substrate used in the electronic device manufacturing apparatus;

(3) the indicator contains a color-changing layer; and (4) the color-changing layer is formed by an ink composition whose color changes or disappears by reaction with at least one member selected from the group consisting of plasma, ozone, ultraviolet rays, and radical-containing gas. The method of the present invention can easily detect whether the above treatment is uniformly performed on an entire semiconductor wafer (in-plane uniformity). Accordingly, it is not necessary to add unnecessary wiring or measuring instruments to an apparatus that performs the above treatment, and evaluation can be conducted in the same manner as in general substrates. Moreover, design guidelines for electronic device manufacturing apparatuses can be obtained. Furthermore, the process management of the manufacturing process can be simplified, thus improving the yield of electronic devices. The method of the present invention includes a single use of the designing method, a single use of the managing method, and a combined use of the designing method and the managing method.

In the present invention, the substrate refers to a base on the surface of which an electronic device is formed.

The material of the substrate (substrate to be treated) is not particularly limited. Examples include silicon, gallium arsenide, silicon carbide, sapphire, glass, gallium nitride, germanium, and the like. In general, (a) when the electronic device is a semiconductor, the substrate is silicon, gallium arsenide, silicon carbide, or the like; (b) when the electronic device is an LED, the substrate is sapphire, gallium nitride, gallium arsenide, or the like; (c) when the electronic device is a semiconductor laser, the substrate is gallium arsenide, gallium nitride, sapphire, or the like; (d) when the electronic device is a power device, the substrate is silicon carbide, gallium nitride, silicon, or the like; (e) when the electronic device is a solar cell, the substrate is silicon, glass, germanium, or the like; (f) when the electronic device is a liquid crystal display, the substrate is glass; and (g) when the electronic device is an organic EL display, the substrate is glass. However, the present invention is not limited to these embodiments (a) to (g).

In the present invention, when the electronic device is a semiconductor, the substrate (i.e., a semiconductor wafer) refers to all semiconductor wafers before being separated into individual semiconductor chips by a dicing process. For example, the semiconductor wafer of the present invention includes any of the following semiconductor wafers: (unprocessed) semiconductor wafers that are raw materials of semiconductor chips, semiconductor wafers obtained after the unprocessed semiconductor wafers are cleaned, semiconductor wafers after a film forming process, semiconductor wafers after a lithography process, semiconductor wafers after an etching process, semiconductor wafers after a flattening process, semiconductor wafers after an electrical property test process, and the like. That is, all semiconductor wafers in the process for sequentially forming patterns to build devices, such as transistors, and wiring correspond to the semiconductor wafer of the present invention. Moreover, when the electronic device is an LED, a semiconductor laser, or a power device, the substrate refers to all substrates before dicing. When the electronic device is a solar cell or an organic EL display, the substrate refers to all substrates before a sealing process. When the electronic device is a liquid crystal display, the substrate refers to all substrates in an array process.

The method of the present invention comprises the step of placing the indicator of the present invention under treatment with at least one member selected from the group consisting of plasma, ozone, ultraviolet rays, and radical-containing gas. Due to this step, the indicator of the present invention is exposed to the above treatment, and the color of the indicator changes or disappears by reaction, thereby allowing the evaluation of the distribution of the above treatment (concentration, flow rate, density, exposure dose, etc.) in the electronic device manufacturing apparatus.

Each of the above treatments when the electronic device is a semiconductor is described in detail below.

Plasma

Plasma is mainly used in the film-forming process, etching process, ashing process, impurity-adding process, cleaning process, etc.

In the film-forming process, for example, a film can be grown on a semiconductor wafer by plasma CVD (chemical vapor deposition) using plasma and heat energy in combination at a low temperature of 400° C. or less at a relatively high growth rate. Specifically, material gas is introduced into a reduced-pressure reaction chamber, and the gas is radically ionized by plasma excitation and reacted. Examples of plasma CVD include capacitive-coupling (anode-coupling or parallel-plate) plasma CVD, inductive-coupling plasma CVD, ECR (electron cyclotron resonance) plasma CVD, etc.

Anther film-forming process is, for example, a film-forming process by sputtering. Specifically, when a voltage of several 10 V to several kV is applied between a semiconductor wafer and a target in inert gas (e.g., Ar) at about 1 Torr to $10^{-4}$ Torr in a high-frequency discharge sputtering device, the ionized Ar accelerates and collides with the target, and the target substance is sputtered and deposited on the semiconductor wafer. At the same time, high-energy $\gamma^-$ electrons are generated from the target to ionize Ar atoms into $Ar^+$ when they collide with the Ar atoms, thereby maintaining the plasma.

Further another film-forming process is, for example, a film-forming process by ion plating. Specifically, after the inside of a processing device is evacuated to a high-vacuum state at about $10^{-5}$ Torr to $10^{-7}$ Torr, inert gas (e.g., Ar) or reactive gas (nitrogen, hydrocarbon, etc.) is introduced, and an electron beam is emitted from a thermionic generation cathode (electron gun) of the processing device to a vapor deposition material, thereby generating plasma in which ions and electrons are separated. Then, after the metal is heated to a high temperature by the electron beam and evaporated, the evaporated metal particles collide with electrons in the plasma by applying a positive voltage to the metal particles, converting the metal particles into positive ions. The metal particles progress toward an object to be treated, while the metal particles and the reactive gas are connected to each other to promote a chemical reaction. The particles in the promoted chemical reaction are accelerated toward the object to be processed, to which negative electrons are added. The particles collide with the object at high energy and are deposited on the surface as metal compounds. Examples of the film-forming process also include evaporation methods similar to ion plating.

Further, examples of the oxidation and nitriding processes include a method of converting the surface of a semiconductor wafer into an oxide film by plasma oxidation using ECR plasma, surface wave plasma, etc.; a method of converting the surface of a semiconductor wafer into a nitride film by introducing ammonia gas, and dissociating, decomposing, and ionizing the ammonia gas by plasma excitation; and the like.

In the etching process, for example, circular plate electrodes are placed in parallel in a reactive ion etching (RIE) device, reactive gas is introduced into a reduced-pressure reaction chamber, the introduced gas is converted into neutral radicals and ions between the electrodes by plasma excitation, and volatile compounds are formed by chemical reaction of these radicals and ions with the material on the semiconductor wafer. The effect of such etching and the effect of physical sputtering are both used. In addition to the above parallel-plate device, a barrel (cylindrical) device can also be used as the plasma etching device.

Another etching process is, for example, reverse sputtering. The principle of reverse sputtering is similar to that of the sputtering mentioned above, and is such that ionized Ar in plasma collides with the semiconductor wafer to perform etching. Further, ion beam etching, which is similar to reverse sputtering, can also be used as the etching process.

In the ashing process, for example, the photoresist is decomposed and volatilized using oxygen plasma generated by plasma excitation of oxygen gas under reduced pressure.

In the impurity-adding process, for example, gas containing impurity atoms to be doped is introduced into a reduced-pressure chamber to excite plasma to ionize impurities, and the impurity ions are doped by applying a negative bias voltage to the semiconductor wafer.

The cleaning process is a process of removing foreign substances adhering to the semiconductor wafer, without damaging the semiconductor wafer, before each process is performed on the semiconductor wafer. Examples include plasma cleaning that performs a chemical reaction with oxygen gas plasma, plasma cleaning that physically removes foreign substances using inert gas (e.g., argon) plasma (reverse sputtering), and the like.

In the designing method and/or managing method of the present invention, the indicator of the present invention can be used in the devices used in each of the above processes. The in-plane uniformity of plasma can thereby be easily detected.

Ozone

Ozone is mainly used in the film-forming process, ashing process, cleaning process, etc.

In the film-forming process, for example, a semiconductor wafer is treated at a high temperature in an ozone gas atmosphere, thereby converting the surface of the semiconductor wafer to an oxide film.

In the ashing process, for example, the photoresist is decomposed and evaporated by a chemical reaction with high-concentration ozone in an ozone ashing device.

The cleaning process is a process of removing foreign substances adhering to the semiconductor wafer, without damaging the semiconductor wafer, before each process is performed on the semiconductor wafer. Examples include ultraviolet-ray cleaning that generates ozone by irradiation with ultraviolet rays, and decomposes and volatilize organic substances. Another example is single-wafer spin cleaning (a method in which substrates are cleaned one by one) that performs cleaning using ozone water or a mixture of ozone gas, water vapor, sulfuric acid, hydrogen peroxide, chlorine, nitric acid, etc.

In the designing method and/or managing method of the present invention, the indicator of the present invention can be used in the devices used in each of the above processes. The in-plane uniformity of ozone can thereby be easily detected.

Ultraviolet Rays

Ultraviolet rays are mainly used in the photolithography process, ashing process, cleaning process, etc.

In exposure to light in the photolithography process (i.e., a process of transferring a mask pattern to a photoresist applied to a semiconductor wafer), the semiconductor wafer is irradiated with ultraviolet rays, which are the light of the light source, through the mask, thereby forming a portion of the photoresist on the semiconductor wafer irradiated with light (corresponding to the transparent portion of the mask) and a portion of the photoresist not irradiated with light (the opaque portion of the mask).

In the ashing process, for example, in a light (excitation) ashing device, ozone etc. are irradiated with ultraviolet rays to generate oxygen radicals, and the photoresist is decomposed and evaporated by chemical reaction, and then discharged.

Examples of the cleaning process include the ultraviolet-ray cleaning described above regarding the cleaning process in the "Ozone" section.

In the designing method and/or managing method of the present invention, the indicator of the present invention can be used in the devices used in each of the above processes. The in-plane uniformity of ultraviolet rays can thereby be easily detected.

Radical-Containing Gas

Radical-containing gas is mainly used in the film-forming process, etching process, ashing process, cleaning process, etc.

Examples of the film-forming process include a method of converting the surface of a semiconductor wafer to an oxide film by oxidizing the semiconductor wafer under reduced pressure using plasma-excited oxygen radicals as an oxidant.

In the ashing process, for example, in a light (excitation) ashing device, ozone etc., are irradiated with ultraviolet rays to generate oxygen radicals, and the photoresist is decomposed and evaporated by chemical reaction, and then discharged.

In the cleaning process, for example, as described above, the semiconductor wafer is irradiated with radical-containing gas containing hydrogen as a raw material, and thereby the natural oxidation film on the wafer substrate surface can be cleaned at a lower temperature than thermal decomposition cleaning.

In the designing method and/or managing method of the present invention, the indicator of the present invention can be used in the devices used in each of the above processes. The in-plane uniformity of radical-containing gas can thereby be easily detected.

Each Treatment on Electronic Devices Other than Semiconductors

When the electronic device is an LED, a semiconductor laser, a power device, or a liquid crystal display, the treatment process includes a film-forming process, a photolithography process, an etching process, an ashing process, a cleaning process, etc., as with when the electronic device is a semiconductor. When the electronic device is a solar cell or an organic EL display, the treatment process includes a film-forming process, a cleaning process, etc., as with when the electronic device is a semiconductor. That is, when the electronic device is an LED, a semiconductor laser, a power device, a liquid crystal display, a solar cell, or an organic EL display, the indicator of the present invention can be used in the devices used in each of the above processes.

The step of placing the indicator of the present invention under the above treatment is preferably performed in an electronic device manufacturing apparatus that performs at least one process selected from the group consisting of oxidation, nitriding, film formation, impurity addition, cleaning, and etching, on a substrate.

When used, the indicator of the present invention may be placed in the installation place of a substrate in each electronic device manufacturing apparatus that performs the above treatment during manufacture of electronic devices. For example, the indicator may be laid in parallel (horizontally) to a wafer stage, heater, vacuum chuck table, etc., or may be placed vertically (or longitudinally) using a wafer boat, etc. These are only examples. This means that the same shape of the indicator as that of the produced substrate does not impose any limitation, and that the indicator can be placed in the same manner as is the substrate. In this case, the indicator placed in the apparatus is exposed to the above treatment, and the color of the indicator changes or disappears; thus, the in-plane uniformity of the treatment can be easily detected.

Advantageous Effects of Invention

The indicator of the present invention can easily detect whether treatment with at least one member selected from the group consisting of plasma, ozone, ultraviolet rays, and radical-containing gas is uniformly performed on an entire substrate (in-plane uniformity).

Moreover, since the designing and/or managing method of the present invention comprises the step of placing the indicator of the present invention under the above treatment, design guidelines for electronic device manufacturing apparatuses can be easily obtained. Furthermore, the above step allows the process management of the manufacturing process, thus improving the yield of electronic devices.

DESCRIPTION OF EMBODIMENTS

The present invention is described in detail below with reference to Examples and Comparative Examples. However, the present invention is not limited to the Examples.

Example 1

Figure 1:
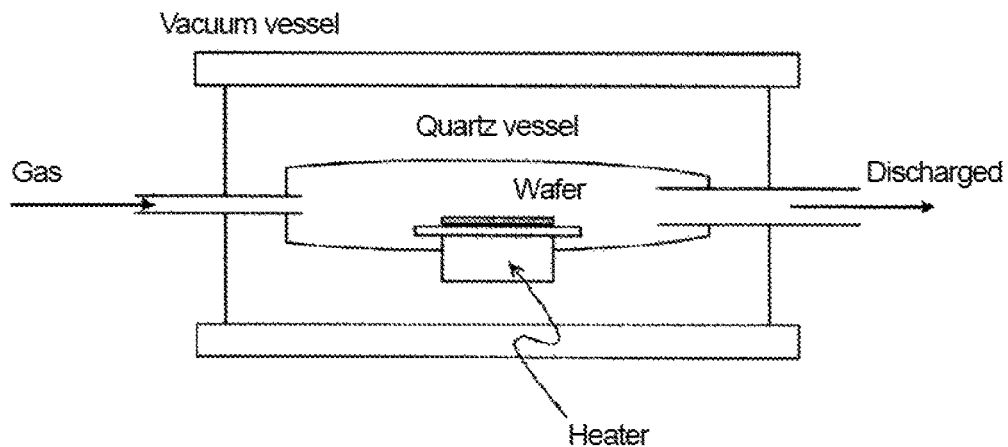
FIG. 1 shows an apparatus for forming oxide films using ozone gas in Example 1.

An example in which the technique of the present invention is applied to an apparatus for forming oxide films using ozone gas is described as Example 1. FIG. 1 shows a schematic diagram of the apparatus. In the apparatus, a quartz reactor is placed in a vacuum vessel, and a silicon wafer (diameter: 200 mm; thickness: 725 μm) is disposed therein and heated by a heater. The reactor also serves as a flow path in which the introduced gas is rectified. Ozone gas in the form of a mixture with oxygen gas is introduced from a gas supply port to oxidize silicon crystals on the surface of the silicon wafer. In this Example, the indicator of the present invention having completely the same shape as that of the silicon wafer was disposed in the apparatus, and the color change of the indicator due to ozone gas was evaluated. The evaluation was carried out by measuring the color difference based on the color of the indicator before treatment. The indicator of Example 1 of the present invention was produced in the following manner. First, components shown in Table 1 were prepared, and the solvent and colorant were stirred and mixed with a dissolver. Subsequently, the resin binders and non-color-changing colorant were supplied, and the mixture was further stirred. The mixture was then returned to ordinary temperature, and the surfactant and extender were added thereto and uniformly stirred, thereby preparing an ink composition. The ink composition was applied to a silicon substrate using a spin coater, and dried at 100° C. for 30 minutes. Thus, the indicator of Example 1 was obtained.

The color difference quantitatively represents the perceptual difference in color. The L*a*b* color system expresses a numerical value ΔE*ab (delta E star a b) defined by the following formula:

$$\Delta E^*ab = [(\Delta L^*)^2 + (\Delta a^*)^2 + (\Delta b^*)^2]^{(1/2)}$$

Figure 2:
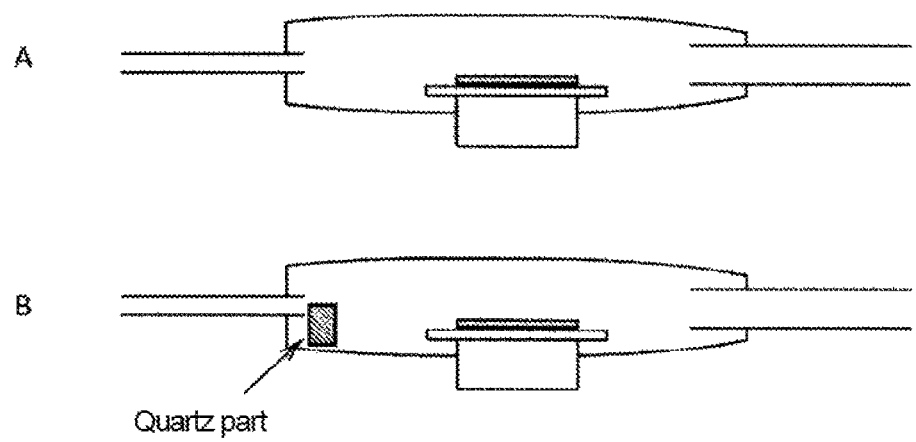
FIG. 2 shows condition A, in which the gas supply port is in a normal state, and condition B, in which a quartz part is placed near the gas supply port, in Example 1.

In this Example, the color difference distribution was compared between condition A, in which the gas supply port was in a normal state, and condition B, in which a quartz part was placed near the supply port, as shown in FIG. 2. Ozone gas was introduced in the form of a mixture with oxygen gas at 500 SCCM for 10 minutes. The indicator was not heated and retained at room temperature.

Figure 3:
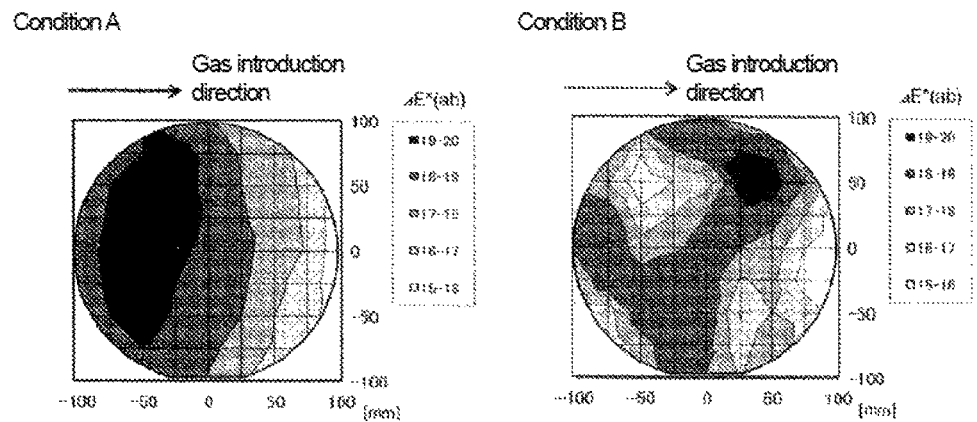
FIG. 3 shows the in-plane distribution of color difference in conditions A and B in Example 1.
Figure 4:
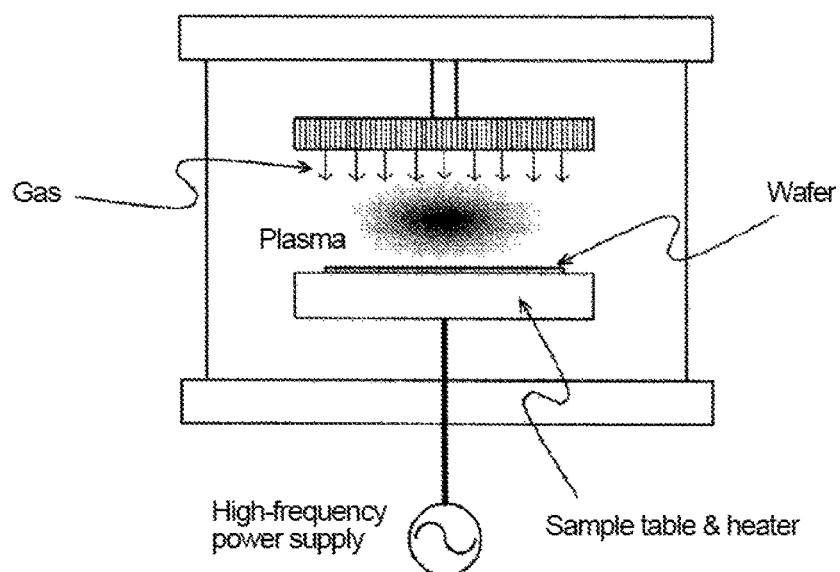
FIG. 4 shows a plasma etching device in Example 2.

FIG. 3 shows the in-plane distribution of the color difference in each condition. The results show that the distribution in condition A was such that the color gradually changed from the supply port toward the discharge port, whereas the distribution in condition B was so complicated that the gas flow was presumably disturbed. The reason for this is considered to be that the quartz part placed in the gas supply port served as an obstacle and caused disturbance of the gas flow, which was originally in a laminar state. The above results demonstrate that regarding the color change of the indicator of the present invention depending on the state of the ozone gas flow, the indicator of the present invention can easily and shortly evaluate the ozone gas flow, which is important in the oxidation process.

Example 2

An example in which the present invention is applied to a plasma etching apparatus is described as Example 2. FIG.

4 shows a schematic diagram of the apparatus. In the apparatus, parallel plate electrodes are placed in a vacuum vessel. The upper electrode has a shower structure, whereby reactive gas is showered on a wafer surface. A silicon wafer (diameter: 200 mm; thickness: 725 μm) is placed on the lower electrode, which is provided with a high-frequency power supply mechanism for plasma excitation, and a heater for heating the wafer. When etching is actually performed, reactive gas is introduced into the vacuum vessel from the shower part of the upper electrode, plasma is generated in the space between the parallel plate electrodes by high-frequency power supplied from the lower electrode, and the generated excited species cause a chemical reaction on the wafer surface to thereby perform etching. In Example 2, the indicator of the present invention having the same shape as that of the wafer was disposed, and carbon tetrafluoride gas ($CF_4$) and argon gas (Ar) were introduced as reactive gases. Then, the color change of the indicator was evaluated. The evaluation was carried out by measuring the color difference based on the color of the indicator before treatment. The indicator of Example 2 of the present invention was obtained in the same manner as in Example 1 after components shown in Table 1 were prepared.

Figure 5:
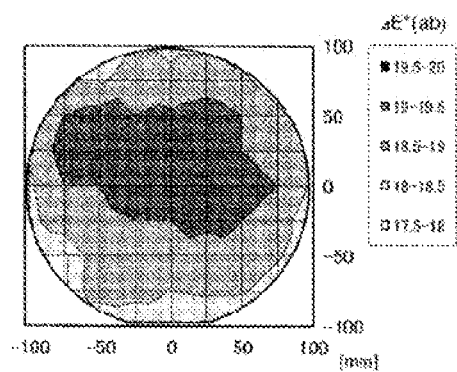
FIG. 5 shows the in-plane distribution of color difference in conditions A and B in Example 2.
Figure 5:
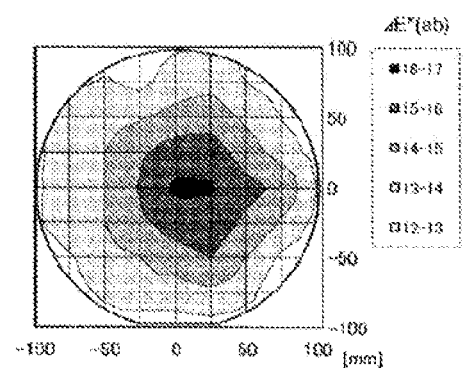

FIG. 5 shows the results. FIG. 5 shows the in-plane distribution of the color change of the indicator depending on the mixing ratio of the two gases. The mixing ratio of the two gases was based on the flow rate of $CF_4$ gas and Ar gas as a parameter. When the flow rate of $CF_4$ gas was 100 SCCM, and the flow rate of Ar gas was 0 SCCM, this case was taken as condition A. When the flow rate of $CF_4$ gas was 50 SCCM, and the flow rate of Ar gas was 50 SCCM, this case was taken as condition B. For both parameters, the high-frequency supply power was 200 W, and the discharge was controlled so that the gas pressure was constant at 10 Pa.

The results demonstrate that the absolute value of the color difference is greater in condition A than in condition B, and that the variation in color difference is smaller in condition A. These results are correlated with etching results obtained by actually treating silicon. That is, it is confirmed that the larger the etching amount, the greater the color difference. Accordingly, the difference in etching conditions can be visually recognized based on the degree and distribution of the color change of the indicator of the present invention. Further, numerical management based on color difference is also possible. Therefore, it is found that the present invention is effective to optimize the process conditions of etching, etc., and can be a simple evaluation method.

TABLE 1

| | Example 1 | Example 2 |
|---|---|---|
| C.I. Basic Red 13 (methine colorant) | 1.60 | |
| C.I. Solvent Red 167:1 (azo colorant) | | 0.3 |
| C.I. Pigment Green 7 (phthalocyanine colorant) | | 0.9 |
| Joncryl 690 (resin binder, produced by Johnson Polymer) | 7.50 | |
| Ethocel 10 (resin binder, produced by Dow Chemical) | 6.50 | |
| Versamid JP802 (polyamide, produced by BASF) | | 10.7 |
| Cyclohexanone | | 13.9 |
| Butyl cellosolve (solvent) | 79.40 | 57.0 |
| Microlith Yellow 3R-T (non-color-changing colorant, produced by Ciba Specialty Chemicals) | 1.00 | |
| Aerosil R-972 (silica, produced by Nippon Aerosil) | 3.00 | 14.3 |
| Nikkol CA-2580 (quaternary ammonium salt surfactant, produced by Nikko Chemicals) | 1.00 | 2.9 |
| Total | 100.00 | 100.00 |

The invention claimed is:

1. An indicator used in an electronic device manufacturing apparatus, wherein:
   (1) the indicator detects at least one member selected from the group consisting of plasma, ozone, ultraviolet rays, and radical-containing gas;
   (2) the indicator has a shape that is the same as that of a substrate used in the electronic device manufacturing apparatus;
   (3) the indicator contains a color-changing layer; and
   (4) the color-changing layer is formed by an ink composition whose color changes or disappears by reaction with at least one member selected from the group consisting of plasma, ozone, ultraviolet rays, and radical-containing gas;
   wherein the indicator is configured to detect by color change or by disappearance of the color-changing layer whether treatment with at least one member selected from the group consisting of plasma, ozone, ultraviolet rays, and radical-containing gas is uniformly performed on the entire substrate in the electronic device manufacturing apparatus.

2. The indicator according to claim 1, which is used in an electronic device manufacturing apparatus that performs at least one process selected from the group consisting of oxidation, nitriding, film formation, impurity addition, cleaning, and etching, on the substrate.

3. The indicator according to claim 1, which contains a non-color-changing layer whose color does not change or disappear by reaction with at least one member selected from the group consisting of plasma, ozone, ultraviolet rays, and radical-containing gas.

4. The indicator according to claim 1, wherein the color-changing layer is formed adjacent to at least one main surface of a base material.

5. The indicator according to claim 3, wherein:
   the non-color-changing layer and the color-changing layer are sequentially formed on a base material;
   the non-color-changing layer is formed adjacent to a main surface of the base material; and
   the color-changing layer is formed adjacent to a main surface of the non-color-changing layer.

6. A method for designing and/or managing an electronic device manufacturing apparatus, wherein:
   (1) the designing and/or managing method comprises the step of placing an indicator that detects at least one member selected from the group consisting of plasma, ozone, ultraviolet rays, and radical-containing gas under treatment with at least one member selected from the group consisting of plasma, ozone, ultraviolet rays, and radical-containing gas;
   (2) the indicator has a shape that is the same as that of a substrate used in the electronic device manufacturing apparatus;
   (3) the indicator contains a color-changing layer; and
   (4) the color-changing layer is formed by an ink composition whose color changes or disappears by reaction with at least one member selected from the group consisting of plasma, ozone, ultraviolet rays, and radical-containing gas.

7. The designing and/or managing method according to claim 6, wherein the step of placing the indicator under the treatment is performed in an electronic device manufacturing apparatus that performs at least one process selected from the group consisting of oxidation, nitriding, film formation, impurity addition, cleaning, and etching, on the substrate.

8. The indicator according to claim 2, which contains a non-color-changing layer whose color does not change or disappear by reaction with at least one member selected from the group consisting of plasma, ozone, ultraviolet rays, and radical-containing gas.

9. The indicator according to claim 2, wherein the color-changing layer is formed adjacent to at least one main surface of a base material.

10. The indicator according to claim 3, wherein the color-changing layer is formed adjacent to at least one main surface of a base material.

\* \* \* \* \*